US010624961B2

(12) United States Patent
Ballou, Jr. et al.

(10) Patent No.: US 10,624,961 B2
(45) Date of Patent: Apr. 21, 2020

(54) METHODS FOR INDUCING AN IMMUNE RESPONSE

(71) Applicant: GLAXOSMITHKLINE BIOLOGICALS SA, Rixensart (BE)

(72) Inventors: William Ripley Ballou, Jr., Rixensart (BE); Arnaud Michel Didierlaurent, Rixensart (BE); Robbert Gerrit Van Der Most, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 313 days.

(21) Appl. No.: 15/300,338

(22) PCT Filed: Apr. 2, 2015

(86) PCT No.: PCT/EP2015/057424
§ 371 (c)(1),
(2) Date: Sep. 29, 2016

(87) PCT Pub. No.: WO2015/150568
PCT Pub. Date: Oct. 8, 2015

(65) Prior Publication Data
US 2017/0136110 A1 May 18, 2017

(30) Foreign Application Priority Data
Apr. 2, 2014 (GB) .................................. 1405921.6

(51) Int. Cl.
*A61K 39/395* (2006.01)
*A61K 39/015* (2006.01)
*A61K 39/04* (2006.01)
*A61K 39/29* (2006.01)
*A61K 39/00* (2006.01)

(52) U.S. Cl.
CPC ............ *A61K 39/015* (2013.01); *A61K 39/04* (2013.01); *A61K 39/292* (2013.01); *A61K 2039/54* (2013.01); *A61K 2039/545* (2013.01); *A61K 2039/55555* (2013.01); *A61K 2039/55572* (2013.01); *A61K 2039/55577* (2013.01); *A61K 2039/575* (2013.01); *A61K 2039/70* (2013.01); *C12N 2730/10134* (2013.01); *Y02A 50/412* (2018.01)

(58) Field of Classification Search
None
See application file for complete search history.

(56) References Cited

U.S. PATENT DOCUMENTS

2009/0136543 A1* 5/2009 Ballou .................. A61K 39/145
424/206.1
2010/0055166 A1* 3/2010 Voss ...................... A61K 39/015
424/450

FOREIGN PATENT DOCUMENTS

WO 2007/068907 A2 6/2007

OTHER PUBLICATIONS

Ballou, W.R., The development of the RTS,S malaria vaccine candidate: challenges and lessons, Parasite Immunol 31(9):492-500.
Gabutti, et al., Booster Vaccination: The Role of Reduced Antigen Content Vaccines as a Preschool Booster, (2014) Biomed Res Int'l 60(1):13-10.
Hill, et al., Vaccines against malaria, (2011) Philosophical Transactions of the Royal Society of London, Series B: Biological Sciences, Royal Society of London, London, GB, 366(1579):2806-2814.
Mata, et al., Malaria Vaccine Adjuvants: Latest Update and Challenges in Preclinical and Clinical Research, (2013) Biomed Res Int'l 6(5):599-519.
Paoletti, et al., Effects of Alum Adjuvant or a Booster Dose on Immunogenicity during Clinical Trials of Group B Streptococcal Type III Conjugate Vaccines, (2001) Infect & Immun 69(11):6696-6701.
Stoute, et al., A Preliminary Evaluation of a Recombinant Circumsporozoite Protein Vaccine against Plasmodium Falciparum Malaria, (1997) New Engl J Med 336(2):86-91.
Stoute, et al., Long-Term Efficacy and Immune Responses Following Immunization with the RTS,S Malaria Vaccine, (1998) J Infect Dis 178(4):1139-1144.
Polhemus, et al., "Evaluation of RTS,S/AS02A and RTS,S/AS01B in Adults in a High Malaria Transmission Area" PLOS One; 2009; pp. 1-12; vol. 4(7).
Ansong, et al., "T cell responses to the RTS,S/AS01(E) and RTS,S/AS02(D) malaria candidate vaccines administered according to different schedules to Ghanaian children" PLoS One; 2011; e18891; vol. 6(4).
Bejon, et al., "Efficacy of RTS,S/ AS01E vaccine against malaria in children 5 to 17 months of age." N Engl J Med; 2008; pp. 2521-2532; vol. 359.
Garcon and Mechelen, "Recent clinical experience with vaccines using MPL- and QS-21-containing adjuvant systems." Expert Rev Vaccines; 2011; pp. 471-486; vol. 10.
Garcon, et al., "GlaxoSmithKline Adjuvant Systems in vaccines; concepts, achievements and perspectives." Expert Rev Vaccines; 2007; pp. 723-739; vol. 6(5).
Hu and Kitagawa, "Studies on the Optimal Immunization Schedule of Experimental Animals. VI. Antigen Dose-Response of Aluminum Hydroxide-aided Immunization and Booster Effect under Low Antigen Dose." Chem Pharm Bull; 1990; pp. 2775; vol. 38(10).
Kester, et al., "Randomized, Double-Blind, Phase 2a Trial of Falciparum Malaria Vaccines RTS,S/AS01B and RTS, S/AS02A in Malaria-Naive Adults: Safety, Efficacy, and Immunologic Associates of Protection." J Infect Dis; 2009; pp. 337-346; vol. 200.
Mettens, et al., "Improved T Cell responses to Plasmodium falciparum circumsporozoite protein in mice and monkeys induced by a novel formulation of RTS,S vaccine antigen." Vaccine; 2008; pp. 1072-1082; vol. 26.
Owusu-Agyei et al., "Randomized Controlled Trial of RTS,S/AS02D and RTS,S/AS01E Malaria Candidate Vaccines Given According to Different Schedules in Ghanaian Children." PLoS; 2009; e7302; pp. 1-11; vol. 4(10).

(Continued)

*Primary Examiner* — Yunsoo Kim
(74) *Attorney, Agent, or Firm* — Virginia G. Campen

(57) ABSTRACT

Methods and uses are provided for inducing an immune response comprising at least two administrations of an immunogenic composition, wherein a lower dose is given in the second administration than in the first administration, and wherein the second administration may be unadjuvanted.

14 Claims, 15 Drawing Sheets

Specification includes a Sequence Listing.

(56) References Cited

OTHER PUBLICATIONS

Polhemus, "Evaluation of RTS,S/AS02A and RTS,S/AS01B in Adults in a High Malaria Transmission Area." PLOS One; 2009; e6465; pp. 1-12; vol. 4(7).
Stevenson and Riley, "Innate Immunity to Malaria" Nature Reviews Immunology; 2004; pp. 169-180; vol. 4.
Tinto, et al. "Efficacy and safety of RTS,S/AS01 malaria vaccine with or without a booster dose in infants and children in Africa: final results of a phase 3, individually randomised, controlled trial." Lancet ; 2015 pp. 31-45.; vol. 386.
Wang et al., Antibody Dynamics of 2009 Influenza A (H1N1) Virus in Infected Patients and Vaccinated People in China, PLOS One, Feb. 9, 2011; e16809; pp. 1-4; vol. 6(2).

* cited by examiner

Figure 2a

```
Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
                20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
                100                 105                 110

Asn Asn Glu Glu Pro Ser Asp Lys His Ile Lys Glu Tyr Leu Asn Lys
        115                 120                 125

Ile Gln Asn Ser Leu Ser Thr Glu Trp Ser Pro Cys Ser Val Thr Cys
    130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
            180                 185                 190

Leu Gly Pro Val Thr Asn Met Glu Asn Ile Thr Ser Gly Phe Leu Gly
```

Figure 2b

```
                195                      200                      205
Pro Leu Leu Val Leu Gln Ala Gly Phe Phe Leu Leu Thr Arg Ile Leu
    210                      215                      220
Thr Ile Pro Gln Ser Leu Asp Ser Trp Trp Thr Ser Leu Asn Phe Leu
225                      230                      235                      240
Gly Gly Ser Pro Val Cys Leu Gly Gln Asn Ser Gln Ser Pro Thr Ser
                245                      250                      255
Asn His Ser Pro Thr Ser Cys Pro Pro Ile Cys Pro Gly Tyr Arg Trp
                260                      265                      270
Met Cys Leu Arg Arg Phe Ile Ile Phe Leu Phe Ile Leu Leu Leu Cys
                275                      280                      285
Leu Ile Phe Leu Leu Val Leu Leu Asp Tyr Gln Gly Met Leu Pro Val
                290                      295                      300
Cys Pro Leu Ile Pro Gly Ser Thr Thr Thr Asn Thr Gly Pro Cys Lys
305                      310                      315                      320
Thr Cys Thr Thr Pro Ala Gln Gly Asn Ser Met Phe Pro Ser Cys Cys
                325                      330                      335
Cys Thr Lys Pro Thr Asp Gly Asn Cys Thr Cys Ile Pro Ile Pro Ser
                340                      345                      350
Ser Trp Ala Phe Ala Lys Tyr Leu Trp Glu Trp Ala Ser Val Arg Phe
                355                      360                      365
Ser Trp Leu Ser Leu Leu Val Pro Phe Val Gln Trp Phe Val Gly Leu
                370                      375                      380
Ser Pro Thr Val Trp Leu Ser Ala Ile Trp Met Met Trp Tyr Trp Gly
385                      390                      395                      400
Pro Ser Leu Tyr Ser Ile Val Ser Pro Phe Ile Pro Leu Leu Pro Ile
                405                      410                      415
```

Figure 2c

```
Phe Phe Cys Leu Trp Val Tyr Ile
            420
```

Figure 3a

<213> VZV gE truncate

<400> 1
Met Gly Thr Val Asn Lys Pro Val Val Gly Val Leu Met Gly Phe Gly
1 5 10 15
Ile Ile Thr Gly Thr Leu Arg Ile Thr Asn Pro Val Arg Ala Ser Val
20 25 30
Leu Arg Tyr Asp Asp Phe His Ile Asp Glu Asp Lys Leu Asp Thr Asn
35 40 45
Ser Val Tyr Glu Pro Tyr Tyr His Ser Asp His Ala Glu Ser Ser Trp
50 55 60
Val Asn Arg Gly Glu Ser Ser Arg Lys Ala Tyr Asp His Asn Ser Pro
65 70 75 80
Tyr Ile Trp Pro Arg Asn Asp Tyr Asp Gly Phe Leu Glu Asn Ala His
85 90 95
Glu His His Gly Val Tyr Asn Gln Gly Arg Gly Ile Asp Ser Gly Glu
100 105 110
Arg Leu Met Gln Pro Thr Gln Met Ser Ala Gln Glu Asp Leu Gly Asp
115 120 125
Asp Thr Gly Ile His Val Ile Pro Thr Leu Asn Gly Asp Asp Arg His
130 135 140
Lys Ile Val Asn Val Asp Gln Arg Gln Tyr Gly Asp Val Phe Lys Gly
145 150 155 160
Asp Leu Asn Pro Lys Pro Gln Gly Gln Arg Leu Ile Glu Val Ser Val
165 170 175
Glu Glu Asn His Pro Phe Thr Leu Arg Ala Pro Ile Gln Arg Ile Tyr
180 185 190
Gly Val Arg Tyr Thr Glu Thr Trp Ser Phe Leu Pro Ser Leu Thr Cys
195 200 205
Thr Gly Asp Ala Ala Pro Ala Ile Gln His Ile Cys Leu Lys His Thr
210 215 220
Thr Cys Phe Gln Asp Val Val Val Asp Val Asp Cys Ala Glu Asn Thr
225 230 235 240
Lys Glu Asp Gln Leu Ala Glu Ile Ser Tyr Arg Phe Gln Gly Lys Lys
245 250 255
Glu Ala Asp Gln Pro Trp Ile Val Val Asn Thr Ser Thr Leu Phe Asp
260 265 270
Glu Leu Glu Leu Asp Pro Pro Glu Ile Glu Pro Gly Val Leu Lys Val
275 280 285
Leu Arg Thr Glu Lys Gln Tyr Leu Gly Val Tyr Ile Trp Asn Met Arg
290 295 300

Figure 3b

```
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
            325                 330                 335
Arg Gly Ala Glu Phe His Met Trp Asn Tyr His Ser His Val Phe Ser
            340                 345                 350
Val Gly Asp Thr Phe Ser Leu Ala Met His Leu Gln Tyr Lys Ile His
            355                 360                 365
Glu Ala Pro Phe Asp Leu Leu Leu Glu Trp Leu Tyr Val Pro Ile Asp
            370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
            405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
            435                 440                 445
Glu Pro Ser Phe Gly Leu Ile Leu His Asp Gly Gly Thr Thr Leu Lys
            450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Val Ser Thr
            485                 490                 495
Val Asp His Phe Val Asn Ala Ile Glu Glu Arg Gly Phe Pro Pro Thr
            500                 505                 510
Ala Gly Gln Pro Pro Ala Thr Thr Lys Pro Lys Glu Ile Thr Pro Val
            515                 520                 525
Asn Pro Gly Thr Ser Pro Leu Ile Arg Tyr Ala Ala Trp Thr Gly Gly
            530                 535                 540
Leu Ala
545
```

Figure 6

Evaluation of Immunogenicity of a delayed &/or a fractional third dose of M72 in WBLO- Pool of peptides M72- PII-PIII

Legend: ◇ Pool 1, ○ Pool 2, □ Pool 3, △ Pool 4, — Median

Y-axis: % of CD4 T cells expressing IL2 &/or IFNg and/or TNF a (medium removed)

| | 7PIII | 7PIII | 7PIII | 7?PIII | 7PIII | 7?PIII | 7PIII | 7PIII | 7PIII | 7PIII | 7PIII |
|---|---|---|---|---|---|---|---|---|---|---|---|
| | 3x 0.25μg M72 AS01E | 3x 0.25μg M72 AS01E | 2x 0.25μg M72 AS01E / 0.05μg M72 AS01E | 2x 0.25μg M72 AS01E / 0.05μg | 2x 0.25μg M72 AS01E / 0.01μg M72 AS01E | 2x 0.25μg M72 AS01E / 0.01μg | 3x 0.25μg M72 AS01E | 2x 0.25μg M72 AS01E / 0.05μg M72 AS01E | 2x 0.25μg M72 AS01E / 0.01μg M72 AS01E | 2x 0.25μg M72 / 0.25μg M72 AS01E alone |
| | | | schedule 0-14-28 | | | | | schedule 0-14-98 | | | |
| Pool 1 | 1.706 | 4.173 | 0.914 | 2.534 | 4.455 | 0.890 | 1.164 | 3.174 | 0.733 | 1.979 | 1.407 | 2.215 | 3.415 | 3.399 | 2.382 |
| Pool 2 | 2.236 | 4.962 | 1.339 | 1.186 | 3.717 | 1.469 | 2.463 | 4.966 | 1.088 | 3.705 | 2.847 | 10.026 | 1.941 | 2.662 | 0.896 |
| Pool 3 | 1.723 | 4.384 | 1.353 | 1.138 | 0.964 | 0.538 | 0.917 | 3.700 | 0.513 | 1.144 | 2.883 | 5.385 | 1.908 | 1.819 | 1.555 |
| Pool 4 | 0.733 | 2.947 | 1.292 | 1.169 | 3.480 | 0.953 | 1.506 | 3.175 | 0.425 | 7.248 | 0.980 | 3.013 | 3.864 | 7.040 | 2.598 |
| Median | 1.714 | 4.279 | 1.315 | 1.178 | 3.599 | 0.921 | 1.335 | 3.438 | 0.623 | 2.842 | 2.127 | 4.199 | 2.678 | 3.030 | 1.968 |

(Note: the last column group "2x 0.25μg M72 / 0.25μg M72 AS01E alone" shows values 4.335, 5.984, 5.249, 9.812, 5.617 for Pool1-4 and Median respectively as second sub-column)

Evaluation of Immunogenicity of a delayed &/or a fractional third dose of M72 in WBLO- Pool of peptides M72- PII-PIII

METHODS FOR INDUCING AN IMMUNE RESPONSE

This application is filed pursuant to 35 U.S.C. § 371 as a United States National Phase Application of International Patent Application Serial No. PCT/EP2015/057424 filed Apr. 2, 2015, which claims priority to United Kingdom Application No. GB 1405921.6 filed Apr. 2, 2014, and the entire contents of each of the foregoing applications are hereby incorporated by reference.

TECHNICAL FIELD

The present invention relates to methods for inducing an immune response, in particular methods for immunisation comprising at least two administrations of an adjuvanted immunogenic composition, wherein a lower dose is given in the second administration than in the first administration.

BACKGROUND OF THE INVENTION

Vaccination is one of the most effective methods for preventing infectious diseases. However, a single administration of an antigen is often not sufficient to confer full immunity and/or a long-lasting response. Approaches for establishing strong and lasting immunity to specific pathogens include addition of adjuvants to vaccines and/or repeated vaccination, i.e. boosting an immune response by administration of one or more further doses of antigen. Such further administrations may be performed with the same vaccine (homologous boosting) or with a different vaccine (heterologous boosting). The most common approach for homologous boosting is not only to administer the same vaccine, but also to administer it in the same dose as the earlier administration.

One disease for which multi-dose vaccination so far has been required is malaria. Malaria is one of the world's major health problems. For the year 2010, the World Health Organization reported an estimated 219 million cases of malaria globally. Malaria is caused by protozoan parasites of the genus *Plasmodium*.

The life cycle of the parasite is complex, requiring two hosts, man and mosquito for completion. The infection of man is initiated by the inoculation of sporozoites through the saliva of an infected mosquito. The sporozoite stage has been identified as one potential target of a malaria vaccine. The major surface protein of the sporozoite is known as circumsporozoite protein (CS protein). RTS,S, an antigen based on the malarial CS protein and a viral envelope protein of the hepatitis B virus, has been under development for more than 25 years and is currently the most advanced malaria vaccine candidate being studied. Its structure and production were described in U.S. Pat. No. 5,928,902, issued 27 Jul. 1999.

In early work, RTS,S was tested in a small clinical trial in combination with an adjuvant comprising QS21 and 3D-MPL associated with an oil-in-water emulsion adjuvant (Stoute et al. 1997 NEJM 336:86). A three full-dose administration schedule had been planned for this study, but because of perceived excess reactogenicity, the third dose was reduced to ⅕ and administered later than originally planned. This study resulted in six out of seven subjects being protected. In subsequent work, a three full-dose immunisation schedule was used and, in more recent studies, also using a three full-dose immunisation schedule, RTS,S was adjuvanted with a liposomal formulation comprising QS21 and 3D-MPL. This adjuvant is termed AS01 and is described e.g. in WO 96/33739 and WO2007/068907. Recent data from a large-scale Phase III clinical trial, wherein RTS,S/AS01 was administered in three identical doses, one month apart, showed that over 18 months of follow-up, RTS,S/AS01 was shown to almost halve the number of malaria cases in young children (aged 5-17 months at first vaccination) and to reduce by around a quarter the malaria cases in infants (aged 6-12 weeks at first vaccination) over a follow-up period of 18 months.

While significant progress has been made in the field of vaccine research and development, there is still a need for novel immunogenic compositions and methods of immunising against diseases, including malaria, which are highly efficacious, safe, cost-effective, long-lasting and induce a broad spectrum of cross-reactive immune responses.

SUMMARY OF THE INVENTION

It has now surprisingly been found that, in a multi-dose method of immunisation using an adjuvanted malaria vaccine, the immunisation was more effective when a subsequent dose (booster dose) was reduced as compared to an earlier dose (primer dose) than when the doses were the same. The adjuvant used comprised a TLR4 agonist, 3D-MPL, and an immunologically active saponin fraction, QS21.

Accordingly, in a first aspect of the invention, there is provided a method for inducing an immune response in a human subject comprising administration of a first immunogenic composition comprising one or more antigens and a first adjuvant to the subject followed by administration of a second immunogenic composition comprising one or more antigens and a second adjuvant to the subject, wherein the first and second composition have at least one antigen in common, wherein the first and second adjuvant comprise a TLR agonist and/or an immunologically active saponin and have at least one of these two components in common and wherein the second adjuvant contains a lower amount of the common component than the first adjuvant, and/or the common antigen is RTS,S and the second composition contains a lower amount of RTS,S than the first composition, with the proviso that the first and second compositions do not both comprise RTS,S and QS21 and 3D-MPL associated with an oil-in-water emulsion formulation.

In a further aspect, there is provided a method for inducing an immune response in a human subject comprising administration of a first immunogenic composition comprising RTS,S and an adjuvant to the subject followed by administration of a second immunogenic composition comprising RTS,S to the subject, wherein the adjuvant comprises a TLR agonist and/or an immunologically active saponin and wherein the second immunogenic composition does not comprise an adjuvant.

BRIEF DESCRIPTION OF THE FIGURES

FIG. 2a-c: The sequence of RTS,S of U.S. Pat. No. 5,928,902, issued 27 Jul. 1999.

FIG. 3a-b: The sequence of the VZV antigen.

FIG. 5a: Subjects not given a booster dose at month 12.

FIG. 6: CD4 T cell responses from mice administered M72 in standard and delayed regimes

BRIEF DESCRIPTION OF THE SEQUENCE IDENTIFIERS

Figure 1:
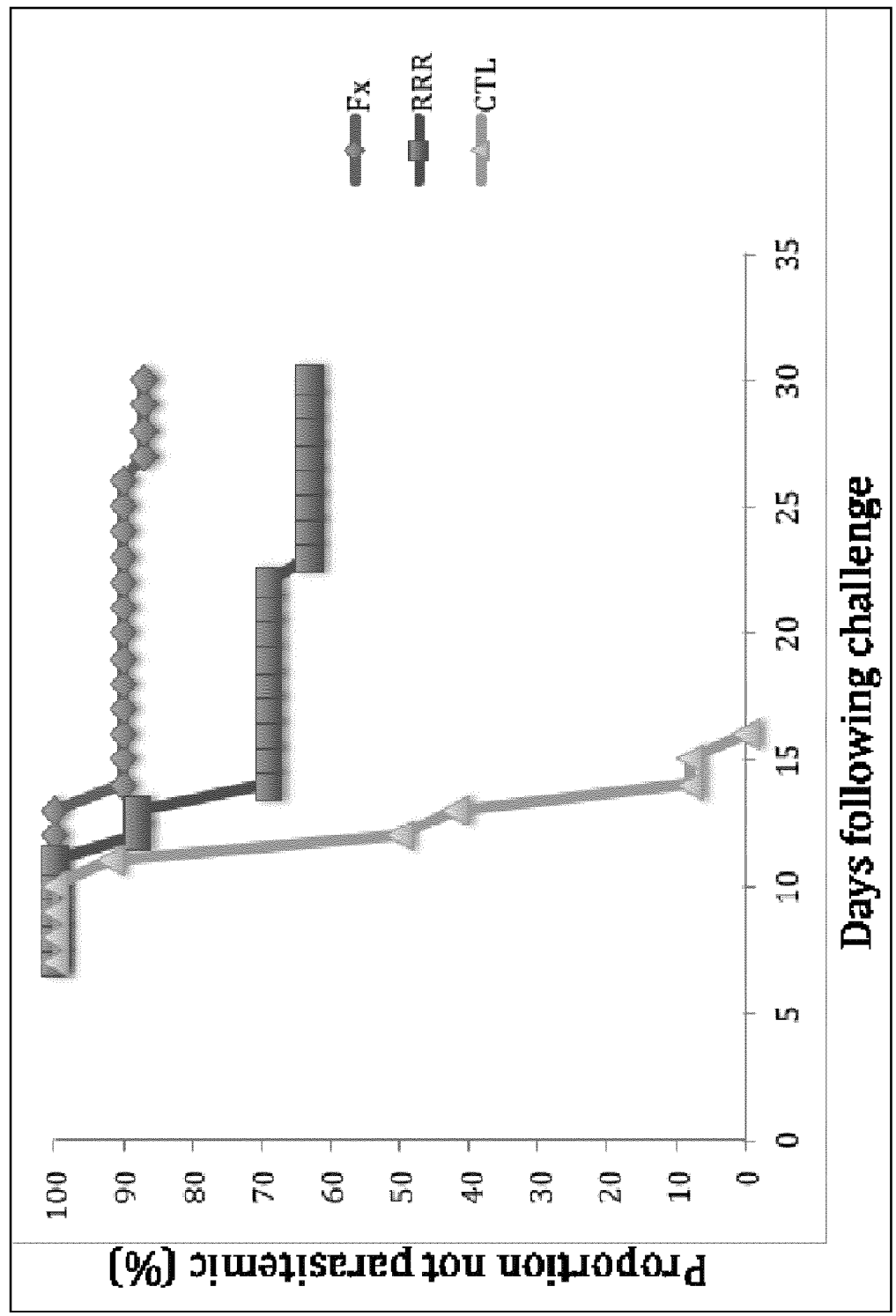
FIG. 1: Percentage of vaccinated subjects who have not developed parasitemia post-challenge over a 28 days follow-up period. Fx indicates the Delayed Fractional Dose group; RRR indicates the 0, 1, 2 month group; CTL indicates the control group.

SEQ ID No. 1: Amino acid sequence of RTS,S, as described elsewhere herein.
SEQ ID No. 2: Amino acid sequence of VZV, as described elsewhere herein.
SEQ ID No. 3: Amino acid sequence of M72, as described elsewhere herein.
SEQ ID No. 4: Amino acid sequence of M72 protein with two N-terminal His residues, as described elsewhere herein.

DETAILED DESCRIPTION

As described above, in a first aspect, the invention relates to a method for inducing an immune response in a human subject comprising administration of a first immunogenic composition comprising one or more antigens and a first adjuvant to the subject followed by administration of a second immunogenic composition comprising one or more antigens and a second adjuvant to the subject, wherein the first and second composition have at least one antigen in common, wherein the first and second adjuvant comprise a TLR agonist and/or an immunologically active saponin and have at least one of these two components in common and wherein
    the second adjuvant contains a lower amount of the common component than the first adjuvant,
    and/or
    the common antigen is RTS,S and the second composition contains a lower amount of RTS,S than the first composition,
with the proviso that the first and second compositions do not both comprise RTS,S and QS21 and 3D-MPL associated with an oil-in-water emulsion formulation.

As used herein, administration of a first composition "followed by" administration of a second composition indicates that a time interval has elapsed between administration of the first composition and administration of the second composition.

Similarly, there is provided a first immunogenic composition for use in a method for inducing an immune response in a human subject, wherein the method comprises administration of a first immunogenic composition comprising one or more antigens and a first adjuvant to the subject followed by administration of a second immunogenic composition comprising one or more antigens and a second adjuvant to the subject, wherein the first and second composition have at least one antigen in common and wherein the first and second adjuvant comprise a TLR agonist and/or an immunologically active saponin and have at least one of these two components in common and wherein
    the second adjuvant contains a lower amount of the common component than the first adjuvant,
    and/or
    the common antigen is RTS,S and the second composition contains a lower amount of RTS,S than the first composition,
with the proviso that the first and second compositions do not both comprise RTS,S and QS21 and 3D-MPL associated with an oil-in-water emulsion formulation.

Similarly, there is provided a second immunogenic composition for use in a method for inducing an immune response in a human subject, wherein the method comprises administration of a first immunogenic composition comprising one or more antigens and a first adjuvant to the subject followed by administration of a second immunogenic composition comprising one or more antigens and a second adjuvant to the subject, wherein the first and second composition have at least one antigen in common, wherein the first and second adjuvant comprise a TLR agonist and/or an immunologically active saponin and have at least one of these two components in common and wherein
    the second adjuvant contains a lower amount of the common component than the first adjuvant,
    and/or
    the common antigen is RTS,S and the second composition contains a lower amount of RTS,S than the first composition,
with the proviso that the first and second compositions do not both comprise RTS,S and QS21 and 3D-MPL associated with an oil-in-water emulsion formulation.

In a further aspect, the invention relates to the use of a second immunogenic composition comprising one or more antigens and a second adjuvant in the manufacture of a medicament for inducing an immune response in a human subject wherein that subject has previously received a first immunogenic composition comprising one or more antigens and a first adjuvant, wherein the first and second composition have at least one antigen in common, wherein the first and second adjuvant comprise a TLR agonist and/or an immunologically active saponin and have at least one of these two components in common and wherein
    the second adjuvant contains a lower amount of the common component than the first adjuvant,
    and/or
    the common antigen is RTS,S and the second composition contains a lower amount of RTS,S than the first composition,
with the proviso that the first and second compositions do not both comprise RTS,S and QS21 and 3D-MPL associated with an oil-in-water emulsion formulation.

In a further aspect, the invention relates to a method for inducing an immune response in a human subject comprising administration of a first immunogenic composition comprising RTS,S and an adjuvant to the subject followed by administration of a second immunogenic composition comprising RTS,S to the subject, wherein the adjuvant comprises a TLR agonist and/or an immunologically active saponin and wherein the second immunogenic composition does not comprise an adjuvant. In one embodiment of this method, the second composition contains a lower amount of RTS,S than the first composition. In one embodiment of this method, the second composition contains equal amounts of RTS,S in the first and second compositions. In one embodiment of this method, the first and the second composition both comprise 25 micrograms of RTS,S or both comprise 50 micrograms of RTS,S.

As described above, in a further aspect, the invention relates to a method for inducing an immune response in a subject comprising administration of a first immunogenic composition comprising one or more antigens and a first adjuvant to the subject followed by administration of a second immunogenic composition comprising one or more antigens and a second adjuvant to the subject, wherein the first and second composition have at least one antigen in common, wherein the first and second adjuvant comprise a TLR agonist and/or an immunologically active saponin and have at least one of these two components in common and wherein the second adjuvant contains a lower amount of the common component than the first adjuvant,
and/or
the common antigen is not RTS,S and the second composition contains a lower amount of the common antigen than the first composition.

In one aspect, the subject is a human subject.

Similarly, there is provided a first immunogenic composition for use in a method for inducing an immune response in a human subject, wherein the method comprises administration of a first immunogenic composition comprising one or more antigens and a first adjuvant to the subject followed by administration of a second immunogenic composition comprising one or more antigens and a second adjuvant to the subject, wherein the first and second composition have at least one antigen in common and wherein the first and second adjuvant comprise a TLR agonist and/or an immunologically active saponin and have at least one of these two components in common and wherein the second adjuvant contains a lower amount of the common component than the first adjuvant,
and/or
the common antigen is not RTS,S and the second composition contains a lower amount of the common antigen than the first composition.

In one aspect, the subject is a human subject.

Similarly, there is provided a second immunogenic composition for use in a method for inducing an immune response in a subject, wherein the method comprises administration of a first immunogenic composition comprising one or more antigens and a first adjuvant to the subject followed by administration of a second immunogenic composition comprising one or more antigens and a second adjuvant to the subject, wherein the first and second composition have at least one antigen in common, wherein the first and second adjuvant comprise a TLR agonist and/or an immunologically active saponin and have at least one of these two components in common and wherein the second adjuvant contains a lower amount of the common component than the first adjuvant,
and/or
the common antigen is not RTS,S and the second composition contains a lower amount of the common antigen than the first composition.

In one aspect, the subject is a human subject.

In a further aspect, the invention relates to the use of a second immunogenic composition comprising one or more antigens and a second adjuvant in the manufacture of a medicament for inducing an immune response in a human subject wherein that subject has previously received a first immunogenic composition comprising one or more antigens and a first adjuvant, wherein the first and second composition have at least one antigen in common, wherein the first and second adjuvant comprise a TLR agonist and/or an immunologically active saponin and have at least one of these two components in common and wherein the second adjuvant contains a lower amount of the common component than the first adjuvant,
and/or
the common antigen is not RTS,S and the second composition contains a lower amount of the common antigen than the first composition.

In one aspect, the subject is a human subject.

In a further aspect, the invention relates to a method for inducing an immune response in a subject comprising administration of a first immunogenic composition comprising an antigen and an adjuvant to the subject followed by administration to the subject of a second immunogenic composition comprising at least one antigen in common with the first composition, wherein the adjuvant comprises a TLR agonist and/or an immunologically active saponin and wherein the second immunogenic composition does not comprise an adjuvant.

In one aspect, the subject is a human subject.

Typically, the aim of the method of the invention is to induce a protective immune response, i.e. immunise or vaccinate the subject against the pathogen from which the antigen is derived. In one embodiment, the vaccine efficacy of the method of the invention is improved as compared to a treatment regimen in which the first composition and the second composition are identical. For example, the vaccine efficacy, as determined according to the Example herein, may be at least 10%, such as 25% improved. In one embodiment, a vaccine efficacy of more than 80%, such more than 90%, as determined according to the Example herein, is achieved. Thus, the method may be used for the prevention (i.e. prophylaxis) of infectious diseases. Alternatively, the method may be used in immunotherapy, i.e. in treatment of a disease, such as cancer, by inducing or enhancing an immune response.

Adjuvants for Use in the Method of the Invention

As described above, in one aspect of the invention, the first adjuvant and second adjuvant comprise a TLR agonist and/or an immunologically active saponin and have at least one of these two components in common.

Thus, in one embodiment, the first adjuvant and second adjuvant both comprise a TLR agonist. In another embodiment, the first adjuvant and second adjuvant both comprise an immunologically active saponin. In yet another embodiment, the first adjuvant and second adjuvant both comprise a TLR agonist and an immunologically active saponin.

In one embodiment, the first adjuvant and the second adjuvant consist of the same components. Thus, in such an embodiment, the components of both adjuvants are the same, although not necessarily in the same relative proportions. For example, the first adjuvant and the second adjuvant may both consists of a TLR agonist and a saponin in a liposomal formulation, but the ratio of TLR agonist to saponin may be 5:1 in the first adjuvant and 1:1 in the second adjuvant. Alternatively, the ratio of TLR agonist to saponin may be 4:1 in the first adjuvant and 1:1 in the second adjuvant, 3:1 in the first adjuvant and 2:1 in the second adjuvant, 1:1 in the first adjuvant and 1:1 in the second adjuvant.

In another embodiment, the first adjuvant and second adjuvant consist of the same components and the relative proportions of these components are the same. However, in such an embodiment, while the relative proportions of the adjuvant components are the same, the absolute amounts of these components may differ between the first and second immunogenic compositions. For example the absolute amounts of all components in the second adjuvant may e.g. be one fifth of the absolute amounts of all components in the first adjuvant.

As described above, in one embodiment, the second adjuvant contains a lower amount of the common component (i.e. a lower amount of the TLR agonist or a lower amount of the saponin or a lower amount of both) than the first adjuvant.

In one embodiment, the lower amount of the common component in the second adjuvant is an at least 10% lower, such as an at least 25% lower, e.g. an at least two fold lower, such as an at least three fold lower, e.g. an at least four fold lower, such as an at least five fold lower, e.g. an at least six fold lower, such as an at least seven fold lower, e.g. an at least eight fold lower, such as an at least nine fold lower, e.g. an at least ten fold lower, such as an at least 15 fold lower, e.g. an at least 20 fold lower amount than in the first adjuvant.

In another embodiment, the lower amount of the common component in the second adjuvant is a between 2 and 50 fold lower, such as a between 2 and 20 fold lower, e.g. such as between 2 and 15 fold lower, such as a between 2 and 10 fold lower, e.g. such as between 3 and 7 fold lower, such as a between 4 and 6 fold lower amount than in the first adjuvant.

As described above, in one embodiment, the first adjuvant and second adjuvant comprise a TLR (Toll-like receptor) agonist. The use of TLR agonists in adjuvants is well-known in art and has been reviewed e.g. by Lahiri et al. (2008) Vaccine 26:6777. TLRs that can be stimulated to achieve an adjuvant effect include TLR2, TLR4, TLR5, TLR7, TLR8 and TLR9. TLR2, TLR4, TLR7 and TLR8 agonists, particularly TLR4 agonists, are preferred.

Suitable TLR4 agonists include lipopolysaccharides, such as monophosphoryl lipid A (MPL) and 3-O-deacylated monophosphoryl lipid A (3D-MPL). U.S. Pat. No. 4,436,727 discloses MPL and its manufacture. U.S. Pat. No. 4,912,094 and reexamination certificate B1 4,912,094 discloses 3D-MPL and a method for its manufacture. Another TLR4 agonist is glucopyranosyl lipid adjuvant (GLA), a synthetic lipid A-like molecule (see, e.g. Fox et al. (2012) Clin. Vaccine Immunol 19:1633). In a further embodiment, the TLR4 agonist may be a synthetic TLR4 agonist such as a synthetic disaccharide molecule, similar in structure to MPL and 3D-MPL or may be synthetic monosaccharide molecules, such as the aminoalkyl glucosaminide phosphate (AGP) compounds disclosed in, for example, WO9850399, WO0134617, WO0212258, WO3065806, WO04062599, WO06016997, WO0612425, WO03066065, and WO0190129. Such molecules have also been described in the scientific and patent literature as lipid A mimetics. Lipid A mimetics suitably share some functional and/or structural activity with lipid A, and in one aspect are recognised by TLR4 receptors. AGPs as described herein are sometimes referred to as lipid A mimetics in the art. In a preferred embodiment, the TLR4 agonist is 3D-MPL.TLR4 agonists, such as 3-O-deacylated monophosphoryl lipid A (3D-MPL), and their use as adjuvants in vaccines has e.g. been described in WO 96/33739 and WO2007/068907 and reviewed in Alving et al. (2012) Curr Opin in Immunol 24:310.

In a further embodiment of the method of the invention, the first adjuvant and the second adjuvant comprise an immunologically active saponin, such as an immunologically active saponin fraction, such as QS21.

Adjuvants comprising saponins have been described in the art. Saponins are described in: Lacaille-Dubois and Wagner (1996) A review of the biological and pharmacological activities of saponins. Phytomedicine vol 2:363. Saponins are known as adjuvants in vaccines. For example, Quil A (derived from the bark of the South American tree Quillaja Saponaria Molina), was described by Dalsgaard et al. in 1974 ("Saponin adjuvants", Archiv. fur die gesamte Virusforschung, Vol. 44, Springer Verlag, Berlin, 243) to have adjuvant activity. Purified fractions of Quil A have been isolated by HPLC which retain adjuvant activity without the toxicity associated with Quil A (Kensil et al. (1991) J. Immunol. 146: 431. Quil A fractions are also described in U.S. Pat. No. 5,057,540 and "Saponins as vaccine adjuvants", Kensil, C. R., Crit Rev Ther Drug Carrier Syst, 1996, 12 (1-2):1-55.

Two such fractions, suitable for use in the present invention, are QS7 and QS21 (also known as QA-7 and QA-21). QS21 is a preferred immunologically active saponin fraction for use in the present invention. QS21 has been reviewed in Kensil (2000) In O'Hagan: Vaccine Adjuvants: preparation methods and research protocols. Homana Press, Totowa, N.J., Chapter 15. Particulate adjuvant systems comprising fractions of Quil A, such as QS21 and QS7, are e.g. described in WO 96/33739, WO 96/11711 and WO2007/068907.

In addition to the other components, the adjuvant preferably comprises a sterol. The presence of a sterol may further reduce reactogenicity of compositions comprising saponins, see e.g. EP0822831. Suitable sterols include beta-sitosterol, stigmasterol, ergosterol, ergocalciferol and cholesterol. Cholesterol is particularly suitable. Suitably, the immunologically active saponin fraction is QS21 and the ratio of QS21:sterol is from 1:100 to 1:1 w/w, such as from 1:10 to 1:1 w/w, e.g. from 1:5 to 1:1 w/w.

In a preferred embodiment of the method of the invention, the TLR4 agonist is 3D-MPL and the immunologically active saponin is QS21.

In some embodiments, the adjuvant is presented in the form of an oil-in-water emulsion, e.g. comprising squalene, alpha-tocopherol and a surfactant (see e.g. WO95/17210) or in the form of a liposome. A liposomal presentation is preferred.

The term "liposome" when used herein refers to uni- or multilamellar (particularly 2, 3, 4, 5, 6, 7, 8, 9, or 10 lamellar depending on the number of lipid membranes formed) lipid structures enclosing an aqueous interior. Liposomes and liposome formulations are well known in the art. Liposomal presentations are e.g. described in WO 96/33739 and WO2007/068907. Lipids which are capable of forming liposomes include all substances having fatty or fat-like properties. Lipids which can make up the lipids in the liposomes may be selected from the group comprising glycerides, glycerophospholipides, glycerophosphinolipids, glycerophosphonolipids, sulfolipids, sphingolipids, phospholipids, isoprenolides, steroids, stearines, sterols, archeolipids, synthetic cationic lipids and carbohydrate containing lipids. In a particular embodiment of the invention the liposomes comprise a phospholipid. Suitable phospholipids include (but are not limited to): phosphocholine (PC) which is an intermediate in the synthesis of phosphatidylcholine;

natural phospholipid derivates: egg phosphocholine, egg phosphocholine, soy phosphocholine, hydrogenated soy phosphocholine, sphingomyelin as natural phospholipids; and synthetic phospholipid derivates: phosphocholine (didecanoyl-L-a-phosphatidylcholine [DDPC], dilauroylphosphatidylcholine [DLPC], dimyristoylphosphatidylcholine [DMPC], dipalmitoyl phosphatidylcholine [DPPC], Distearoyl phosphatidylcholine [DSPC], Dioleoyl phosphatidylcholine, [DOPC], 1-palmitoyl, 2-oleoylphosphatidylcholine [POPC], Dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero-3-phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-distearoyl-sn-glycero-3-phosphoethanolamine [DSPE], 1,2-Dioleoyl-sn-Glycero-3-Phosphoethanolamine [DOPE]), phoshoserine, polyethylene glycol [PEG] phospholipid.

Liposome size may vary from 30 nm to several um depending on the phospholipid composition and the method used for their preparation. In particular embodiments of the invention, the liposome size will be in the range of 50 nm to 500 nm and in further embodiments 50 nm to 200 nm. Dynamic laser light scattering is a method used to measure the size of liposomes well known to those skilled in the art.

In a particularly suitable embodiment, liposomes used in the invention comprise DOPC and a sterol, in particular cholesterol. Thus, in a particular embodiment, compositions of the invention comprise QS21 in any amount described herein in the form of a liposome, wherein said liposome comprises DOPC and a sterol, in particular cholesterol.

Preferably, the first adjuvant and second adjuvant comprise 3D-MPL and QS21 in a liposomal formulation.

In one embodiment, the first adjuvant comprises between 25 and 75, such as 50 micrograms, of 3D-MPL and between 25 and 75, such as 50 micrograms of QS21 in a liposomal formulation and the second adjuvant comprises between 5 and 15, such as 10 micrograms of 3D-MPL and between 5 and 15, such as 10 micrograms of QS21 in a liposomal formulation.

In another embodiment, the first adjuvant comprises between 12.5 and 37.5, such as 25 micrograms, of 3D-MPL and between 12.5 and 37.5, such as 25 micrograms of QS21 in a liposomal formulation and the second adjuvant comprises between 2.5 and 7.5, such as 5 micrograms of 3D-MPL and between 2.5 and 7.5, such as 5 micrograms of QS21 in a liposomal formulation.

In another embodiment, the first adjuvant comprises between 12.5 and 37.5, such as between 20 and 30 micrograms (for example about or exactly 25 micrograms) of 3D-MPL and between 12.5 and 37.5, such as between 20 and 30 micrograms (for example about or exactly 25 micrograms) of QS21 in a liposomal formulation and the second adjuvant comprises a reduced amount of 3D-MPL or QS21, such as between 2.5 and 20, such as between 2.5 and 10 micrograms (for example about or exactly 5 micrograms) of 3D-MPL and such as between 2.5 and 20, such as between 2.5 and 10 micrograms (for example about or exactly 5 micrograms) of QS21 in a liposomal formulation. Suitably in first and second adjuvants the amount of 3D-MPL is the same as the amount of QS21.

It is well known that for parenteral administration solutions should be physiologically isotonic (i.e. have a pharmaceutically acceptable osmolality) to avoid cell distortion or lysis. A pharmaceutically acceptable osmolality will generally mean that solutions will have an osmolality which is approximately isotonic or mildly hypertonic. Suitably the immunogenic compositions of the present invention will have an osmolality in the range of 250 to 750 mOsm/kg, for example, the osmolality may be in the range of 250 to 550 mOsm/kg, such as in the range of 280 to 500 mOsm/kg. Osmolality may be measured according to techniques known in the art, such as by the use of a commercially available osmometer, for example the Advanced® Model 2020 available from Advanced Instruments Inc. (USA). An "isotonicity agent" is a compound that is physiologically tolerated and imparts a suitable tonicity to a formulation (e.g. immunogenic compositions of the invention) to prevent the net flow of water across cell membranes that are in contact with the formulation. Aqueous adjuvant compositions are known which contain 100 mM sodium chloride or more, for example adjuvant system A (ASA) in WO 2005/112991 and WO2008/142133 or the liposomal adjuvants disclosed in WO2007/068907.

In some embodiments, the isotonicity agent used for the composition is a salt. In other embodiments, however, the composition comprises a non-ionic isotonicity agent and the concentration of sodium chloride or the ionic strength in the composition is less than 100 mM, such as less than 80 mM, e.g. less than 30 mM, such as less 10 mM or less than 5 mM. In a preferred embodiment, the non-ionic isotonicity agent is a polyol, such as sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2010142685, see e.g. Examples 1 and 2 in WO2010142685.

In a further embodiment, first adjuvant and/or the second adjuvant does not comprise aluminium.

Antigens for Use in the Methods of the Invention.

In one embodiment of the method of the invention, second composition contains a lower amount of the common antigen than the first composition.

In one embodiment, the lower amount of common antigen in the second composition is an at least 10% lower, such as an at least 25% lower, e.g. an at least two fold lower, such as an at least three fold lower, e.g. an at least four fold lower, such as an at least five fold lower, e.g. an at least six fold lower, such as an at least seven fold lower, e.g. an at least eight fold lower, such as an at least nine fold lower, e.g. an at least ten fold lower, such as an at least 15 fold lower, e.g. an at least 20 fold lower amount of antigen than in the first composition.

In another embodiment, the lower amount of common antigen in the second composition is a between 2 and 50 fold lower, such as a between 2 and 20 fold lower, e.g. such as between 2 and 15 fold lower, such as a between 2 and 10 fold lower, e.g. such as between 3 and 7 fold lower, such as a between 4 and 6 fold lower amount of antigen than in the first composition.

As described above, the first immunogenic composition and the second immunogenic composition have at least one antigen in common. In some embodiments, all antigens in the first and second compositions are the same.

In one embodiment, the common antigen is a *Plasmodium* antigen, such as a *P. falciparum* or a *P. vivax* antigen. In one embodiment, the common antigen is circumsporozoite (CS)

protein or an immunogenic fragment or variant thereof, such as the CS protein of *P. falciparum* or an immunogenic fragment or variant thereof or CS protein of *P. vivax* or an immunogenic fragment or variant thereof.

In another embodiment, the common antigen is CelTOS (Genbank Accession number Q8I5P1: *P. falciparum* 3D7 CelTOS; also GenBank: AAN36249).), TRAP (Genbank Accession:CAD52497.1 GI:23615505) or Pfs25 (Genbank Accession number: AAN35500.1 GI:23495169) or an immunogenic fragment or variant of CelTOS, TRAP, and/or Pfs25.

In a further embodiment, the common antigen is an immunogenic protein consisting of the surface antigen S from hepatitis B (HBsAg) or an immunogenic fragment thereof or an immunogenic protein comprising HBsAg or an immunogenic fragment thereof, e.g. a fusion protein of HBsAg with a different antigen.

In a further embodiment, the common antigen is a VZV (varicella-zoster virus) antigen. An example of a VZV antigen is the VZV glycoprotein gE (also known as gp1) or immunogenic derivative hereof. The wild type or full length gE protein consists of 623 amino acids comprising a signal peptide, the main part of the protein, a hydrophobic anchor region (residues 546-558) and a C-terminal tail. In one aspect, a gE C-terminal truncate (also referred to truncated gE or gE truncate) is used whereby the truncation removes 4 to 20 percent of the total amino acid residues at the carboxy terminal end. In a further aspect, the truncated gE lacks the carboxy terminal anchor region (suitably approximately amino acids 547-623 of the wild type sequence). In a further aspect gE is a truncated gE having the sequence of SEQ ID NO. 2.

The gE antigen, anchorless derivatives thereof (which are also immunogenic derivatives) and production thereof is described in EP0405867 and references therein (see also Vafai (1994) Vaccine 12:1265). EP192902 also discloses gE and production thereof. Truncated gE having the sequence set forth in SEQ ID No. 2, is also disclosed by Haumont et al. Virus Research (1996) 40:199, herein incorporated fully by reference.

In a further embodiment, the common antigen is a cytomegalovirus (CMV) antigen, such as the gB or an immunogenic fragment or variant thereof. Suitable gB derived antigens have been described in WO 2012/049317, which published in the US as US2013216613 and which is incorporated by reference for the purpose of describing suitable proteins for use in the present invention In a further embodiment, the common antigen is an Respiratory Syncytial Virus (RSV) antigen, such as the F protein of RSV or an immunogenic fragment or variant thereof. Suitable F protein derived antigens have been described in WO2010149745, e.g. the F protein variants set forth in SEQ ID NO:18, SEQ ID NO:20 and SEQ ID NO:22 in WO2010149745. Other suitable RSV antigens have been described in WO2011008974 and WO2012158613.

In a further embodiment, the common antigen is a dengue virus antigen, such as an inactivated or live-attenuated whole dengue virus. The composition may be multivalent and e.g. contain four or more dengue strains.

In a further embodiment, the common antigen is a *Haemophilus influenzae* antigen, such as Protein E and/or Pilin A or immunogenic fragments or variants thereof, e.g. those described in WO2012139225.

In a further embodiment, the common antigen is a *M. tuberculosis* antigen, such as the M72 antigen, e.g. the antigen described in WO2006/117240, which granted as U.S. Pat. No. 8,470,338 and which is incorporated by reference for the purpose of describing suitable proteins for use in the present invention.

*M. tuberculosis* antigens of interest include sequences comprising (or consisting of):
  Rv0125, also known as Mtb32a, such as described in SEQ ID No 20 or 21 of WO2010010177;
  Rv0915, also known as MTCC2 or Mtb41, such as described in SEQ ID No 14 of WO2010010177;
  Rv1174, also known as DPV, such as described in SEQ ID No 8 of WO2010010177;
  Rv1196, also known as Mtb39 or TbH9, such as described in SEQ ID No 13 of WO2010010177;
  Rv1753, such as described in SEQ ID Nos 1 and 2-7 of WO2010010180;
  Rv1793, also known as MTI or Mtb9.9, such as described in SEQ ID No 10 of WO2010010177;
  Rv2087, also known as MSL or Mtb9.8, such as described in SEQ ID No 9 of WO2010010177;
  Rv2386, such as described in SEQ ID Nos 1 and 2-7 of WO2010010179;
  Rv3616, also known as HTCC1 or Mtb40, such as described in SEQ ID Nos 1 and 2-7 WO2010010177 or SEQ ID Nos 161-169, 179 or 180 of WO2011092253;
or comprising (or consisting of) immunogenic fragments of at least 20 (such as at least 50) residues of any of the above sequences or comprising (or consisting of) variants having at least 90% (such as at least 95% or 98%) identity of any of the above sequences.

*M. tuberculosis* fusion antigens of interest include those derived from Mtb72f, as described in SEQ ID No 23 of WO2010010177; or M72, as described in SEQ ID No. 3 herein. M72 antigens of particular interest are those comprising (or consisting of) an amino acid sequence having at least 90% (such as at least 95% or 98%) identity to SEQ ID No. 3 herein, such as sequences comprising residues 2 to 723 of SEQ ID No. 3 (for example SEQ ID No. 4 herein).

Other *M. tuberculosis* antigens of interest include sequences comprising (or consisting of):
  ESAT-6 (also known as esxA and Rv3875) the polypeptide sequence of which is described in SEQ ID No: 103 of WO97/09428 (cDNA in SEQ ID No: 104) and in Sorensen et al *Infection and Immunity* 1995 63(5): 1710-1717. The full-length polypeptide sequence for ESAT-6 is shown in SEQ ID No: 16 of WO10010180;
  Ag85 complex antigens (e.g. Ag85A, also known as fbpA and Rv3804c; or Ag85B, also known as fbpB and Rv1886c) which are discussed, for example, in Content et al *Infection and Immunity* 1991 59:3205-3212 and in Huygen et al *Nature Medicine* 1996 2(8):893-898. The full-length polypeptide sequence for Ag85A is shown in SEQ ID No: 17 of WO10010180 (the mature protein of residues 43-338, i.e. lacking the signal peptide, being of particular interest). The full-length polypeptide sequence for Ag85B is shown in SEQ ID No: 18 of WO10010180 (the mature protein of residues 41-325, i.e. lacking the signal peptide, being of particular interest);
  Alpha-crystallin (also known as hspX and Rv2031c) which is described in Verbon et al *Journal of Bacteriology* 1992 174:1352-1359 and Friscia et al *Clinical and Experimental Immunology* 1995 102:53-57 (of particular interest are the fragments corresponding to residues 71-91, 21-40, 91-110 and 111-130). The full-length polypeptide sequence for alpha-crystallin is shown in SEQ ID No: 19 of WO10010180;

Mpt64 (also known as Rv1980c) which is described in Roche et al *Scandinavian Journal of Immunology* 1996 43:662-670. The full-length polypeptide sequence for MPT64 is shown in SEQ ID No: 20 of WO10010180 (the mature protein of residues 24-228, i.e. lacking the signal peptide, being of particular interest):

TB10.4, the full-length polypeptide sequence for TB10.4 is shown in SEQ ID No: 23 of WO10010180;

or comprising (or consisting of) immunogenic fragments of at least 20 (such as at least 50) residues of any of the above sequences or comprising (or consisting of) variants having at least 90% (such as at least 95% or 98%) identity of any of the above sequences.

An immunogenic fragment can be of any length provided that it retains immunogenic properties. For example, the fragment can comprise 5 or more consecutive amino acids, such as 10 or more consecutive amino acids, e.g. 20 or more consecutive amino acids, such as 50 or more consecutive amino acids, e.g. 100 or more consecutive amino acids of the relevant protein.

In a further embodiment, the common antigen comprises or consists of a variant of the relevant protein.

A variant polypeptide may contain a number of substitutions, preferably conservative substitutions, (for example, 1-50, such as 1-25, in particular 1-10, and especially 1 amino acid residue(s) may be altered) when compared to the reference sequence. Suitably such substitutions do not occur in the region of an epitope, and do not therefore have a significant impact on the immunogenic properties of the antigen.

Protein variants may also include those wherein additional amino acids are inserted compared to the reference sequence, for example, such insertions may occur at 1-10 locations (such as 1-5 locations, suitably 1 or 2 locations, in particular 1 location) and may, for example, involve the addition of 50 or fewer amino acids at each location (such as 20 or fewer, in particular 10 or fewer, especially 5 or fewer). Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Variants also include those wherein amino acids have been deleted compared to the reference sequence, for example, such deletions may occur at 1-10 locations (such as 1-5 locations, suitably 1 or 2 locations, in particular 1 location) and may, for example, involve the deletion of 50 or fewer amino acids at each location (such as 20 or fewer, in particular 10 or fewer, especially 5 or fewer). Suitably such deletions do not occur in the region of an epitope, and do not therefore have a significant impact on the immunogenic properties of the antigen.

The skilled person will recognise that a particular protein variant may comprise substitutions, deletions and additions (or any combination thereof).

Variants preferably exhibit at least about 70% identity, more preferably at least about 80% identity and most preferably at least about 90% identity (such as at least about 95%, at least about 98% or at least about 99%) to the associated reference sequence.

Examples of algorithms that are suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively.

A suitable variant of the CS protein may be a variant wherein parts of the CS protein are in the form of a hybrid protein with the surface antigen S from hepatitis B (HBsAg). The CS variant antigen may e.g. be in the form of a hybrid protein comprising substantially all the C-terminal portion of the CS protein, four or more tandem repeats of the CS protein immunodominant region, and HBsAg. The hybrid protein may comprise a sequence which contains at least 160 amino acids and which is substantially homologous to the C-terminal portion of the CS protein, but devoid of the hydrophobic anchor sequence. The CS protein may be devoid of the last 12 amino-acids from the C terminal. Further, it may contain 4 or more e.g. 10 or more Asn-Ala-Asn-Pro tetrapeptide (NANP) repeat motifs.

The hybrid protein for use in the invention may be a protein which comprises a portion of the CS protein of *P. falciparum* substantially as corresponding to amino acids 207-395 of *P. falciparum* clone 3D7, derived from the strain NF54 fused in frame via a linear linker to the N-terminus of HBsAg. The linker may comprise a portion of preS2 from HBsAg. CS constructs suitable for use in the present invention are outlined in WO 93/10152, which granted in the US as U.S. Pat. Nos. 5,928,902 and 6,169,171, both of which are incorporated by reference for the purpose of describing suitable proteins for use in the present invention.

Figure 2C:
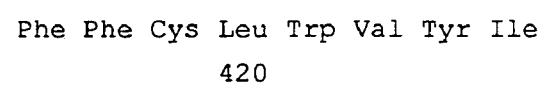

A particular hybrid protein for use in the invention is the hybrid protein known as RTS (FIG. 2 and SEQ ID No. 1) (described in WO93/10152 (wherein it is denoted RTS* and in WO98/05355) which consists of:
  a methionine residue
  three amino acid residues, Met Ala Pro
  a stretch of 189 amino acids representing amino acids 207 to 395 of the CS protein of *P. falciparum* strain 3D7
  an glycine residue
  four amino acid residues, Pro Val Thr Asn, representing the four carboxy terminal residues of the hepatitis B virus (adw serotype) preS2 protein, and
  a stretch of 226 amino acids, encoded by nucleotides 1653 to 2330, and specifying the S protein of hepatitis B virus (adw serotype).

RTS may be in the form of RTS,S mixed particles. RTS,S particles comprise two polypeptides, RTS and S, that may be synthesized simultaneously and spontaneously form composite particulate structures (RTS,S).

The RTS protein may be expressed in yeast, for example *S. cerevisiae*. In such a host, RTS will be expressed as lipoprotein particles. The recipient yeast strain may already carry in its genome several integrated copies of a hepatitis B S expression cassette. The resulting strain synthesizes therefore two polypeptides, S and RTS, that spontaneously co-assemble into mixed (RTS,S) lipoprotein particles. These particles may present the CS protein sequences of the hybrid at their surface. The RTS and S in these mixed particles may be present at a particular ratio, for example 1:4.

RTS,S has been reviewed in e.g. Vekemans et al. (2009) Vaccine 275:G67 and Regules et al. (2011) Expert Rev. Vaccines 10:589.

In one embodiment, the first immunogenic composition comprises between 25 and 75, such as 50 micrograms, of RTS,S and the second immunogenic composition comprises between 5 and 15, such as 10 micrograms of RTS,S.

In another embodiment, the first immunogenic composition comprises between 12.5 and 37.5, such as 25 micrograms, of RTS,S and the second immunogenic composition comprises between 2.5 and 7.5, such as 5 micrograms of RTS,S.

In a further embodiment, the common antigen is derived from the CS protein of *P. vivax*. Suitable *P. vivax* CS protein variants have been described. For example, WO2008009652, which published in the US as US20100150998 and is incorporated by reference for the purpose of purpose of describing suitable proteins for use in the present invention, describes immunogenic hybrid fusion proteins comprising: a. at least one repeat unit derived from the repeating region of a type I circumsporozoite protein of *P. vivax*, b. at least one repeat unit derived from the repeating region of a type II circumsporozoite protein of *P. vivax*, and c. surface antigen S derived from Hepatitis B virus, or a fragment thereof. SEQ ID NO:17 of WO2008009652 describes a specific hybrid fusion protein, termed CSV-S. When co-expressed with surface antigen S derived from hepatitis B virus, CSV-S,S particles, are formed (WO2008009652). Such particles may also be used in the present invention.

In a further embodiment, the common antigen is a mixed particle comprising RTS and CSV-S. Such particles have been described in WO2008009650, which published in the US as US20100062028 and is incorporated by reference for the purpose of purpose of describing suitable proteins for use in the present invention.

Immunisation Regimes, Target Populations and Modes of Administration

As described above, the method of the invention comprising administration of a first immunogenic composition comprising one or more antigens and a first adjuvant followed by administration of a second immunogenic composition comprising one or more antigens and a second adjuvant.

In one embodiment, the time interval between the initial administration of the first composition and administration of the second composition is between 1 and 24 months, e.g. between 1 and 18 months, such as between 1 and 12 months, e.g. between 2 and 24 months, e.g. between 2 and 18 months, such as between 2 and 14 months, such as between 2 and 12 months, between 2 and 10 months, such as between 3 and 9 months, e.g. between 4 and 8 months, such as between 7 and 8 months.

In another embodiment, the time interval between the initial administration of the first composition and administration of the second composition is accelerated, such that the time interval between the initial administration of the first composition and administration of the second composition is between 1 and 28 days, e.g., between 1 and 21 days, e.g., between 1 and 14 days, e.g. between 1 and 7 days.

The method of the invention may comprise one or more further administrations of immunogenic compositions in addition to the initial administration of the first composition and the administration of the second composition. For example, the subject may receive multiple doses of the first composition before administration of the second composition. Thus, for example, in one embodiment, the first composition is administered twice before administration of the second composition. Alternatively or in addition, the subject may receive multiple further doses of the second composition after the initial administration of the second composition. Accordingly, in one embodiment of the method of the invention, the second composition is administered one or more further times. Possible regimens thus include, but are not limited to, the following:

a. First composition then second composition
b. First composition then first composition then second composition
c. First composition then second composition then second composition
d. First composition then first composition then first composition then second composition
e. First composition then first composition then second composition then second composition
f. First composition then second composition then second composition then second composition Time intervals for regimen b. could e.g. be 0, 1, 5 (i.e. Month 0, Month 1, Month 5) or 0, 1, 6 or 0, 1, 7 or 0, 1, 8 or 0, 1, 12. Similarly, time intervals for regimen c. could e.g. be 0, 1, 5 or 0, 1, 6 or 0, 1, 7 or 0, 1, 8 or 0, 1, 12. Accelerated intervals for regimens b. and c. could e.g. be Day 0, Day 7, Day 14.

In a further embodiment, the second composition could e.g. be given as a recurrent yearly booster, e.g. for 1-5 years or more. In one embodiment, at a time interval of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, or more months after administration of the second composition, the second composition is administered one or more further times. In one embodiment, at a time interval of at least 1, at least 2, at least 3, at least 4, at least 5 years after administration of the second composition, the second composition is administered one or more further times.

The subject to be treated using the method of the invention may be of any age. In one aspect of the invention, the subject is human. The method of the invention could be used as part of an elimination program for malaria in which case immunisation of essentially the whole population, i.e. all or the majority of age groups, might be useful. In one embodiment, however, the human subject is more than 18 years of age when the first composition is administered. In another embodiment, the human subject is less than five years of age when the first composition is administered. In a further embodiment, the subject is aged 6-12 weeks or 5-17 months. A further particularly suitable target population includes travellers to regions where malaria is endemic.

The first and second compositions may be administered via various suitable routes, including parenteral, such as intramuscular or subcutaneous administration.

In one particular embodiment, the second composition is administered intradermally. The term intradermally as used herein is intended to refer to the application of antigens into the dermis and/or epidermis of human skin. Intradermal application of an immunogenic composition may be performed by using any cutaneous method known to the skilled person including, but not limited to, delivery using a short needle device (a device comprising a microneedle that is between about 0.2 and about 0.6 mm in length) or delivery using a skin patch. Suitable devices for use with the cutaneous vaccines described herein include short needle devices such as those described in U.S. Pat. Nos. 4,886,499, 5,190,521, 5,328,483, 5,527,288, 4,270,537, 5,015,235, 5,141,496, 5,417,662 and EP1092444. Cutaneous vaccines may also be administered by devices which limit the effective penetration length of a needle into the skin, such as those described in WO99/34850. Also suitable are jet injection devices which deliver liquid vaccines to the dermis via a liquid jet injector or via a needle. Also suitable are ballistic powder/particle delivery devices which use compressed gas to accelerate vaccine in powder form through the outer layers of the skin to the dermis. Skin patches will generally comprise a backing plate which includes a solid substrate. Patches deliver the antigen and adjuvant used in the invention to the dermis or epidermis. In particular embodiment, the patches useful in the present invention comprise a plurality of microprojections. The microprojections may be of any shape suitable for piercing the stratum corneum, epidermis and/or dermis and delivery and antigen and adjuvant to the epidermis or dermis. In a particular embodiment, microprojections are biodegradable and comprise a biodegradable polymer.

Immunogenic compositions used in the invention may be made by admixing the antigen(s) and the adjuvant. The antigen(s) may be provided in a lyophilized form or in a liquid formulation. For each composition, a kit may be provided comprising a first container comprising the antigen and a second container comprising the adjuvant.

Suitably, the immunogenic compositions according to the present invention have a human dose volume of between 0.05 ml and 1 ml, such as between 0.1 and 0.5 ml, in particular a dose volume of about 0.5 ml, or 0.7 ml. The volume of the second immunogenic composition may be reduced, and e.g. be between 0.05 ml and 0.5 ml, such as between 0.1 and 0.2 ml. The volumes of the compositions used may depend on the delivery route with smaller doses being given by the intradermal route.

Typically for administration to humans the first and second immunogenic compositions will comprise between 1 ug and 100 ug of *M. tuberculosis* antigen (e.g. a polypeptide comprising SEQ ID No. 3), such as between 1 ug and 50 ug. Suitably the first immunogenic composition will contain between 1 ug and 50 ug of M72 related antigen (such as between 5 ug and 50 ug), especially between 1 ug and 20 ug (such as between 5 ug and 20 ug) and in particular around or exactly 10 ug.

In some embodiments the second immunogenic composition will contain the same amount of M72 related antigen as the first immunogenic composition. For example, the second immunogenic composition will contain between 1 ug and 50 ug of M72 related antigen (such as between 5 ug and 50 ug), especially between 1 ug and 20 ug (such as between 5 ug and 20 ug) and in particular around or exactly 10 ug.

In other embodiments the second immunogenic composition will contain a reduced amount of M72 related antigen relative to the first immunogenic composition. For example, the second immunogenic composition will contain between 1 ug and 40 ug of M72 related antigen (such as between 2 ug and 40 ug), especially between 1 ug and 16 ug (such as between 2 ug and 16 ug) and in particular less than 10 ug (such as 1 to 8 ug).

The teaching of all references in the present application, including patent applications and granted patents, are herein fully incorporated by reference. A composition or method or process defined as "comprising" certain elements is understood to encompass a composition, method or process (respectively) consisting of those elements. The invention will be further described by reference to the following, non-limiting, example:

Example 1: Vaccination Using RTS,S and Adjuvant AS01 and Experimental Malaria Challenge Vaccine Used in the Study RTS,S was produced in yeast (*S. cerevisiae*) essentially as described in WO 93/10152.

A "standard" dose of RTS,S/AS01 contains 50 ug of lyophilised RTS,S antigen reconstituted in 500 uL of AS01 adjuvant containing the immunostimulants 3D-MPL® (GlaxoSmithKline Biologicals, Montana, USA) and QS21 (50 ug of each) in a formulation with liposomes.

A "fractional" dose of RTS,S/AS01 is 100 uL of the above solution, i.e. containing 10 ug of lyophilised RTS,S antigen and 10 ug of each of 3D-MPL and QS21 with liposomes.

TERMINOLOGY

Herein, the standard dose of RTS,S/AS01 is referred to as "R", whereas the fractional dose is referred to as "r". A standard regimen of three standard doses is referred to as "RRR", whereas the regimen in which the third dose is fractional is referred to as "RRr." A regimen with two standard doses followed by two fractional doses would be "RRrr," and so on.

Methodology

A clinical trial was performed to evaluate the safety, reactogenicity and efficacy against sporozoite challenge of a malaria vaccine containing the antigen RTS,S adjuvanted with AS01, administered intramuscularly in healthy malaria-nave volunteers aged 18-50 years. The "Delayed Fractional Dose" group was given in two standard doses, at 0 and 1 month, and a fractional dose (one fifth ($1/5^{th}$) of the standard dose) at 7 months. The ("0, 1, 2-month" group) was given three standard doses one month apart.

46 subjects were recruited into two cohorts and were randomized in the above-referred to "Delayed Fractional Dose" (30 subjects) and "0, 1, 2-month" groups (16 subjects). 12 more subjects were part of "infectivity" control, i.e. volunteers who did not receive any immunization, but underwent the sporozoite challenge.

For each cohort, volunteers were requested to undergo a standardised primary malaria challenge (Chulay et al. (1986) Am J Trop Med Hyg. 35:66), also commonly known as "sporozoite challenge", about 3 weeks following the third dose of any of the above group. The primary challenge involved allowing five *P. falciparum* sporozoite infected *Anophelese stevensi* mosquitos to feed on each challenge volunteer for a period of five minutes.

After the challenge subjects were followed daily for a period of at least 30 days to assess whether they had become infected with malaria. The principle method of detecting infection was an evaluation of a Giesma-stained peripheral blood smear to detect asexual stage parasites by light microscopy. The presence of asexual stage parasites indicates that a subject has undergone a productive infection, with parasites having been released from the liver and progressed to erythrocytic stage and thus that sterile protection against challenge has not been achieved.

At the first sign of infection subjects were declared to be positive for malaria and received a curative dose of chloroquine. The primary efficacy readout was sterile protection, i.e. the subject never developed asexual stage parasitaemia. In addition, the time between the challenge and the appearance of parasitaemia in those that were not fully protected was recorded. Protection was evaluated by the proportion of immunized participants who remain free of *P. falciparum* infection following sporozoite challenge and by a delay in the pre-patent period leading to infection.

Vaccine efficacy (VE) was defined as 100*(1-Relative Risk). Fisher's Exact test was used for the comparison of malaria incidence between each one of the "Delayed Fractional Dose" and "0, 1, 2-month" vaccine groups and "infectivity" controls.

Results

TABLE 1

Vaccine Efficacy

| Groups | Number of subjects vaccinated | Number of vaccinated subjects who developed parasitemia post-challenge** | Vaccine Efficacy % (VE) Estimate* |
|---|---|---|---|
| Delayed Fractional Dose | 30 | 4 | 87 |
| 0, 1, 2-month | 16 | 6 | 63 |

*Logrank analysis (time to parasitemia), Fx over RRR p = 0.0455.
**Parasitemia has been measured at Day 28 post-challenge.

Figure 4A:
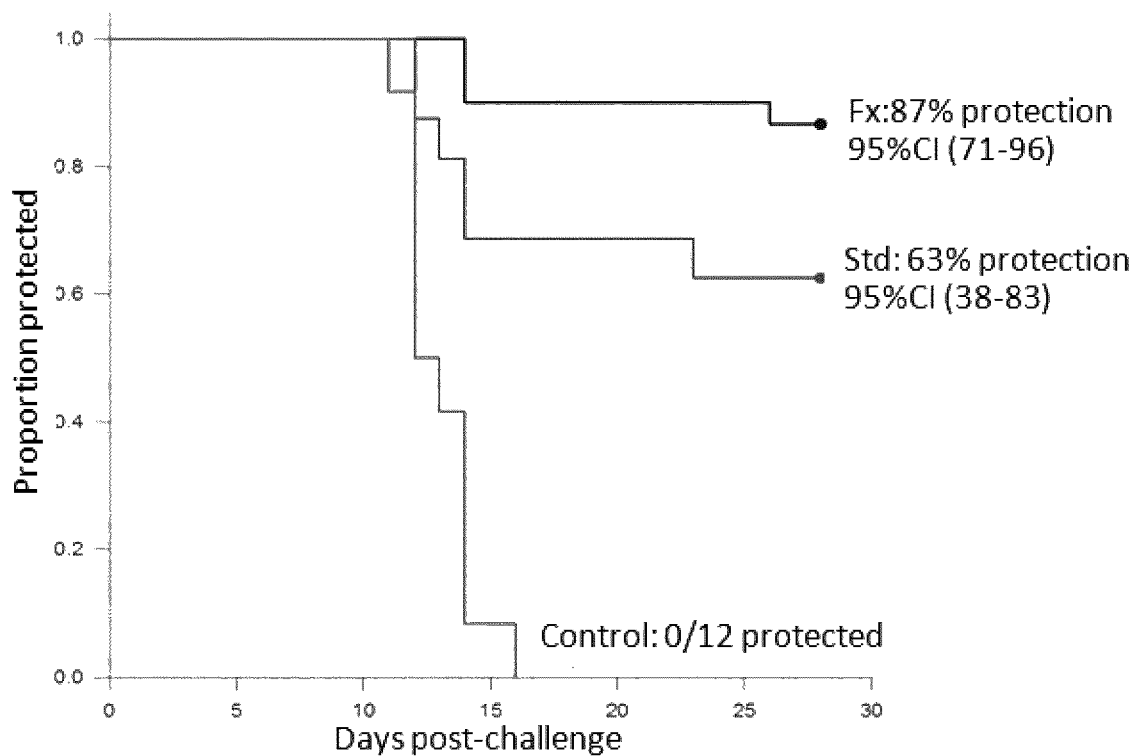
FIG. 4a: 4/30 subjects in the RRr group developed parasitemia (VE=87% [95% CI: 67, 95]); 6/16 subjects in the RRR group developed parasitemia (VE=63% [95% CI 20, 80]).
Figure 4B:
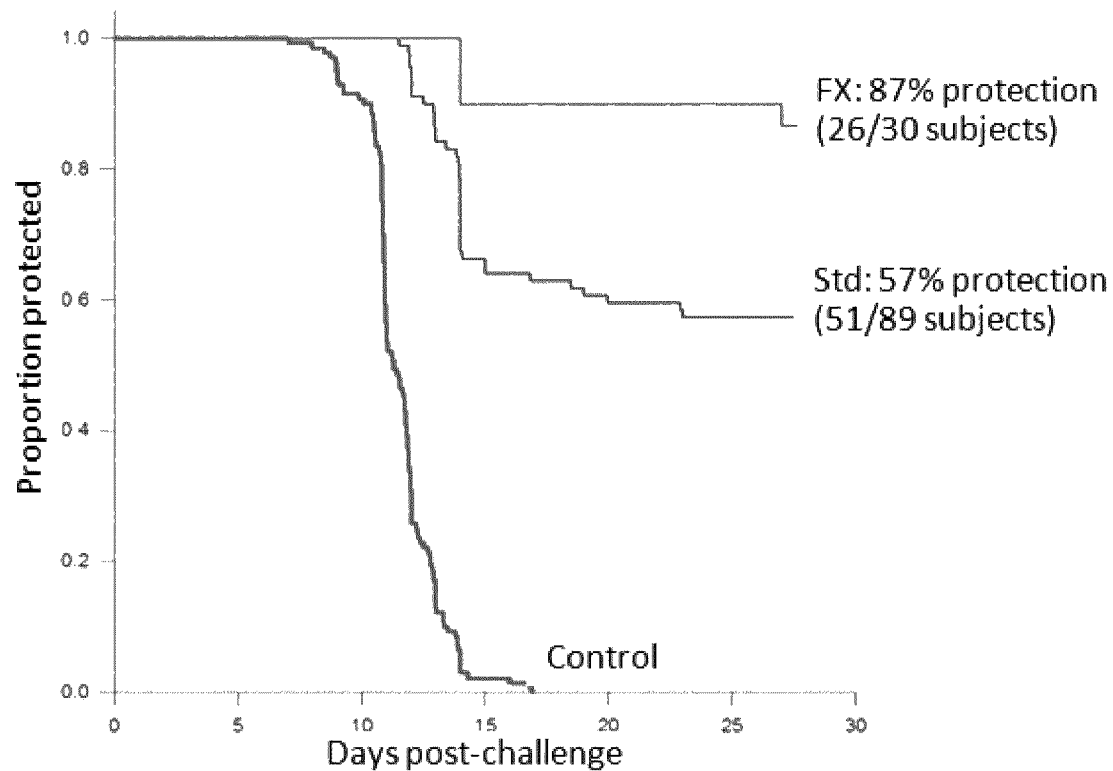
FIG. 4b: An analysis comparing the results of the Delayed Fractional Dose arm of the study against the pooled data for 95 subjects studied in five 0, 1, 2 month RTS,S/AS01 trials completed to date.

The study was not powered to detect superiority of the Delayed Fractional Dose group over the 0, 1, 2 month group, and the difference between the two groups is not quite statistically significant (VE increase of Fx over RRR=57.0%, [−7.9–88.3], p=0.0741, Fisher's exact). However, an analysis of difference in survival time of the Delayed Fractional Dose group over the 0, 1, 2 month group, which takes into account the delay in time to infection in the Delayed Fractional Dose group, does reach statistical significance (p=0.0455, logrank): 4/30 subjects in the RRr group developed parasitemia (VE=87% [95% CI: 67, 95]); 6/16 subjects in the RRR group developed parasitemia (VE=63% [95% CI 20, 80]). FIG. 4a. Furthermore, an analysis comparing the results of the Delayed Fractional Dose arm of the study against the pooled data for 95 subjects studied in five 0, 1, 2 month RTS,S/AS01 trials completed to date indicates that the current results are highly unlikely to have happened by chance (p=0.0045, Fisher's exact). FIG. 4b.

Study Extension

Figure 5A:
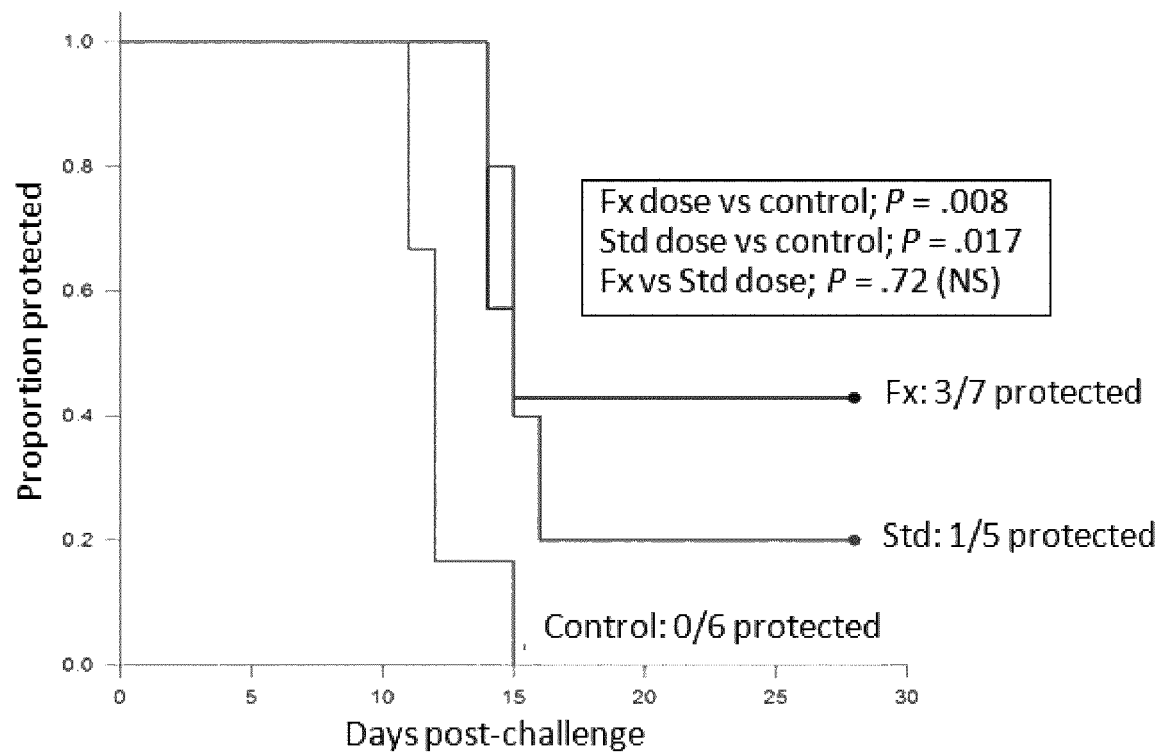
FIGS. 5a-b: Study of a fractional boost 6 months after the last dose followed by sporozoite challenge a month later. Subjects who were unprotected following the first challenge were offered a fractional boost. Subjects who were protected after the first challenge were randomized to receive or not receive a fractional boost, followed by sporozoite challenge a month later.
Figure 5B:
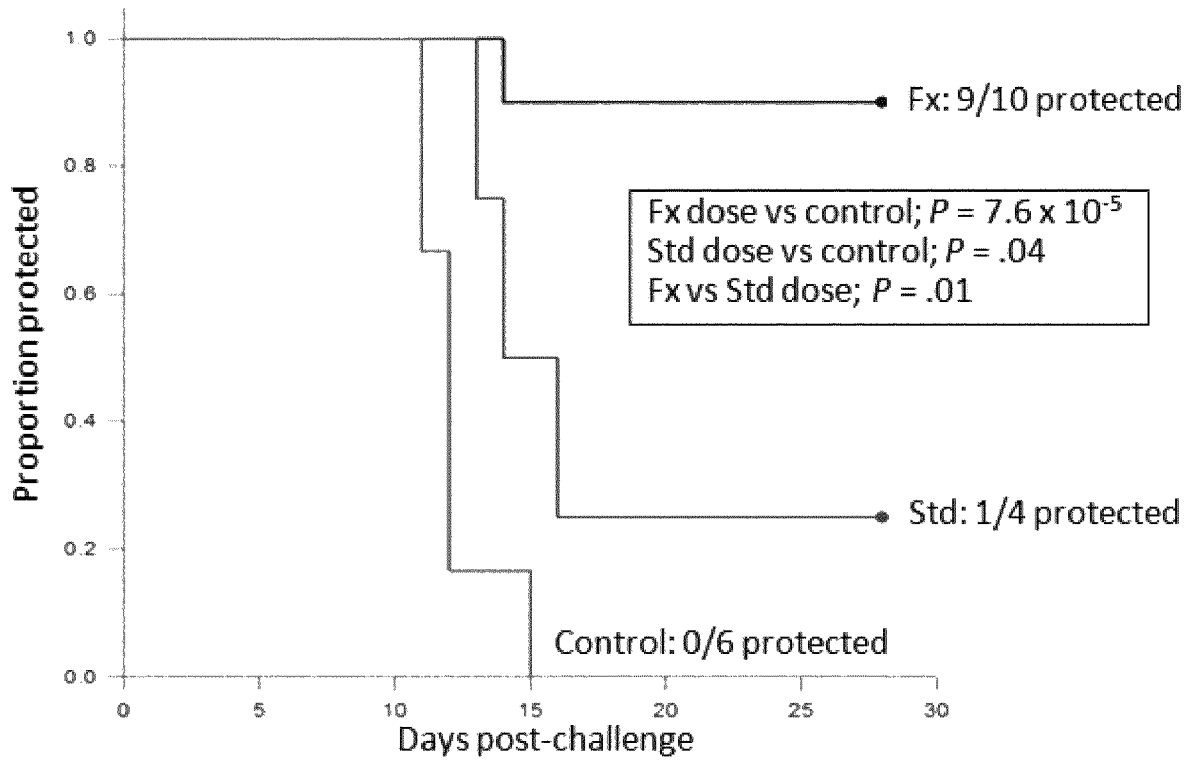

The study was extended and some subjects received a fractional boost 6 months after the last dose followed by sporozoite challenge a month later. Subjects who were unprotected following the first challenge were offered a fractional boost. Subjects who were protected after the first challenge were randomized to receive or not receive a fractional boost, followed by sporozoite challenge a month later. Results are summarized in Table 2 and FIGS. 5a and 5b. NP stands for not protected during the first challenge, P stands for Protected during the first challenge. All boosts were fractional (a fifth of a dose of RTS,S/AS01B).

TABLE 2

Fractional dose booster.

| Regimen | Protected |
|---|---|
| RRr- NP- Boosted | 2/2 |
| RRr - P - Boosted | 9/10 |
| RRr - P - No Boost | 3/7 |
| RRR - NP - Boosted | 2/3 |
| RRR - P - Boosted | 1/5 |
| RRR - P - No Boost | 1/4 |
| Infectivity Control | 0/6 |

The majority of subjects not protected after either the Fx regimen (n=2) or standard dose regimen of RTS,S (n=3) can be protected with subsequent booster dose (⅕th dose) (data not shown).

Anti-CS Antibody Titers

Anti-CS antibody titers were determined by standard enzyme-linked immunosorbent assay (ELISA) developed by GSK Biologicals. Clement et al. (2012) *Malar J* 11:384. Antibody titers were calculated using a reference standard curve and expressed in ELISA units (EU) as described. Results are summarized in Table 3.

TABLE 3

Anti-CS antibody titers. Fx, RRR, NP, P, Fx NP, Fx P, RRR NP and RRR P are as described elsewhere herein.

| CATEGORY | N | GMT | LL | UL |
|---|---|---|---|---|
| Fx | 30 | 40545 | 32979 | 49847 |
| RRR | 16 | 55148 | 37072 | 82037 |
| NP | 10 | 39800 | 22368 | 70817 |
| P | 36 | 46725 | 38432 | 56808 |
| Fx NP | 4 | 34583 | 19060 | 62748 |
| Fx P | 26 | 41549 | 33231 | 51944 |
| RRR NP | 6 | 43708 | 17505 | 109133 |
| RRR P | 10 | 63403 | 44880 | 89570 |

Avidity Assay

The avidity index (AI) of the anti-CS antibodies against the repeat region of CSP was assessed. For measurements of avidity of IgG, samples were evaluated as described in Olotu et al (2014) *PLoS One* 15; 9(12):e115126. doi: 10.1371/journal.pone.0115126 using two different ELISA plates; one treated with a chaotropic agent and one untreated plate. As chaotropic agent a 1 M solution of ammonium thiocyanate (NH4SCN) was added in the treatment plate while 0.05% Tween-20 in PBS was added in the untreated plate and both ELISA plates were further washed and developed as described. The avidity index (AI) was calculated as the ratio of the concentration of anti-CSP IgG (EU/ml) that remained bound to the coated antigen after treatment with NH4SCN, divided by the concentration of IgG (EU/ml) that remained bound to the coated antigen in the untreated plate. Results are summarized in Table 4.

TABLE 4

Avidity Index (AI). Fx, RRR, NP, P, Fx NP, Fx P, RRR NP and RRR P are as described elsewhere herein.

| CATEGORY | N | GMT | LL | UL |
|---|---|---|---|---|
| Fx | 30 | 0.68 | 0.65 | 0.72 |
| RRR | 16 | 0.55 | 0.51 | 0.58 |
| NP | 10 | 0.61 | 0.55 | 0.68 |
| P | 36 | 0.64 | 0.61 | 0.68 |
| Fx NP | 4 | 0.70 | 0.63 | 0.78 |
| Fx P | 26 | 0.68 | 0.64 | 0.72 |
| RRR NP | 6 | 0.55 | 0.50 | 0.60 |
| RRR P | 10 | 0.54 | 0.49 | 0.59 |

AI may be utilzed for comparison of regimens but does not explain protection at individual level.

Example 2: Vaccination Using M72 and Adjuvant AS01

The impact of delayed and reduced dosages of the tuberculosis antigen M72 2-his (SEQ ID No. 4) was investigated in a mouse model.

Material and Methods

Animal Model

Female mouse C57BL/6JOlaHsd—6 weeks old—12 mice per group—were injected by the intramuscular route with 50 µl at days 0-14 and 28 or 98 as indicated in table below.

| Group | Dose 1<br>D 0 | Dose 2<br>D 14 | Dose3<br>D 28 | Dose3<br>D 98 |
|---|---|---|---|---|
| G1 | 0.25 ug M72<br>AS01E | 0.25 ug M72<br>AS01E | 0.25 ug M72<br>AS01E | |
| G2 | | | 0.05 ug M72<br>1/5$^{th}$ AS01E | |
| G3 | | | 0.01 ug M72<br>1/25$^{th}$ AS01E | |
| G4 | | | | 0.25 ug M72<br>AS01E |
| G5 | | | | 0.05 ug M72<br>1/5$^{th}$ AS01E |
| G6 | | | | 0.01 ug M72<br>1/25$^{th}$ AS01E |
| G7 | | | | 0.25 ug M72<br>alone |

AS01E adjuvant contained the immunostimulants 3D-MPL® (GlaxoSmithKline Biologicals, Montana, USA) and QS21 (2.5 ug of each) in a formulation with liposomes. Dilutions were performed using the adjuvant buffer.

Read-out:
Whole Blood ICS at
day 21—7 days Post-II (G1-7);
day 35—7 days Post-III (G1-3);
day 105—77 days Post-III (G1-3) and 7 days Post-III (G4-7)
Serology anti-M72 IgTot at
day 28—14 days Post-II (G1-7)
day 42—14 days Post-III (G1-3)
day 112—84 days Post III (G1-3) and 14 days Post III (G4-7)

In order to have sufficient volume, the whole blood of 4 pools of 3 mice for groups was collected at days 21, 35 and 105. Individual sera were collected at days 28, 42 and 112.

The mice were individually identified in order to link PII and PIII results for ICS and serology.

Read-Out(s) Description
Cellular Immune Response-Intracellular Cytokine Staining (ICS)
Leukocyte Isolation At each time point, blood was collected from each mouse and subsequently pooled (5 pools of 3 mice). Blood was collected in tubes containing, RPMI/additives (RPMI 1640, supplemented with Glutamine, Penicillin/streptomycin, Sodium Pyruvate, non-essential amino-acids and 2-mercaptoethanol) containing heparin (1/10). Ten volumes of Lysing buffer were added to the whole blood and tubes were incubated at room temperature (RT) for 10 min. After centrifugation (335 g, 10 min at RT), the pellet was harvested in RPMI/additives and filtered (Cell strainer 100 μm). Cells were pelleted again (335 g, 10 min at RT) and resuspended in Complete Medium (RPMI 1640, supplemented with Glutamine, Penicillin/streptomycin, Sodium Pyruvate, non-essential amino-acids and 2-mercaptoethanol, and 5% Heat inactivated Fetal Calf Serum).

In Vitro Stimulation of Fresh Leukocytes

Leukocytes were plated in round bottom 96-well plates at approximately 1 million cells per well. Leukocytes were then stimulated for 6 hours (37° C., 5% CO2) with anti-CD28 (clone 9C10 (MFR4.B) and anti-CD49d (clone 37.51) at 1 μg/ml, with or without 1 μg/ml of peptides covering the M72 sequence. After a 2 hour-stimulation, Brefeldin A diluted 1/200 in complete medium was added for 4 additional hours. Plates were then transferred at 4° C., overnight.

ICS

Cells were stained and analyzed using a 5-colour ICS assay.

Cells were transferred to V-bottom 96-well plates, centrifuged at 189 g for 5 min at 4° C. after wash with 200 μl Flow Buffer (PBS 1×, 1% FCS), resuspended the cells in 50 μl Flow Buffer containing anti-CD16/32 (clone 2.4G2) diluted 1/50, for 10 min at 4° C. Then, 50 μl Flow Buffer containing anti-CD4-V450 (clone RM4-5, diluted 1/50) and anti-CD8-PerCp-Cy5.5 (clone 53-6.7, diluted 1/50) antibodies and Live&Death PO (diluted 1/500) was added for 30 min at 4° C. Cells were centrifuged (189 g for 5 min at 4° C.) and washed with 200 μl Flow Buffer.

Leukocytes were fixed and permeabilized by adding 200 μl of Cytofix/Cytoperm solution (Becton Dickinson commercial buffer) for 20 min at 4° C. Cells were centrifuged (189 g for 5 min at 4° C.) and washed with 200 μl Perm/Wash buffer (Becton Dickinson commercial buffer diluted 1:10 in distilled water). After an additional centrifugation step, cells were stained in 50 μl Perm/Wash buffer with anti-IL2-FITC (clone JES6-5H4, diluted 1/400), anti-IFNγ-APC (clone XMG1.2, diluted 1/50) and anti-TNFα-PE (clone MP6-XT22, diluted 1/700) antibodies, for 1 hour at 4° C. Cells were washed twice with the Perm/Wash buffer resuspended in 220 μl BD Stabilizing Fixative solution. Stained cells were analyzed by flow cytometry using a LSRII and the FlowJo software.

Humoral Response—Anti-M72 Ig Tot Serology by ELISA 96-well Elisa plates were coated with the recombinant antigen M72 at 0.25 μg/ml in PBS and incubated overnight at 4° C. Sera from vaccinated mice at Post II and Post III were diluted at 1/10000, in PBS (0.2%)-BSA and then a 2 fold serial dilution is performed from well 1 to 12 and incubated. Serial dilutions of the standard and control material were used to calculate the anti-M72 antibody standard titers of tested sera and to ensure validity of the test. Plates were washed with PBS 0.1% tween 20 buffer after each incubation step. A biotinylated goat antibody specific for mice Ig is then added and the antigen-antibody complex is revealed by incubation with a streptavidin-peroxidase complex and a peroxidase substrate ortho-phenylenediamine dihydrochlorid/H2O2. The Optical densities (O.D.) were recorded at 490-620 nm. The anti-M72 antibody titer of each individual mouse serum is determined from the standard curve of the ELISA using a regression model and expressed in ELISA unit (EU)/ml. Geometric Mean Titers (GMT) are then calculated for each group of mice.

Results
T Cell Responses
A. Kinetics of the M72-Specific CD4 T & CD8 T Cells Responses To evaluate a potential benefit of the fractional and/or or delayed third dose on the CD4 T and CD8 T cell response, mice were immunized with a maximal dose of 0.25 ug M72 in the current study in order to be in the dynamic range of the CD4 T cell response while inducing a detectable CD8 T cell response.

As shown in FIG. 6, giving a fractional third dose in the standard schedule (D0-D14-D28) did not provide an improved CD4 T cell response as comparable boosts were observed from 7PII to 7PIII in groups receiving a full dose, 1/5$^{th}$ and 1/25$^{th}$ of the dose.

However, despite some variability of the M72 specific CD4 T cell response between pools, a greater boost was observed 7 days after a delayed third dose of 0.25 ug of M72 as compared to the standard schedule. Furthermore, the level of M72 specific CD4 T cell response in mice receiving a delayed and fractional third dose or a delayed and unadjuvanted third dose was comparable to the levels observed in group immunized with the full dose in the standard schedule. This suggests a benefit of a delayed schedule in terms of the level of the CD4 T cell response.

Figure 8:
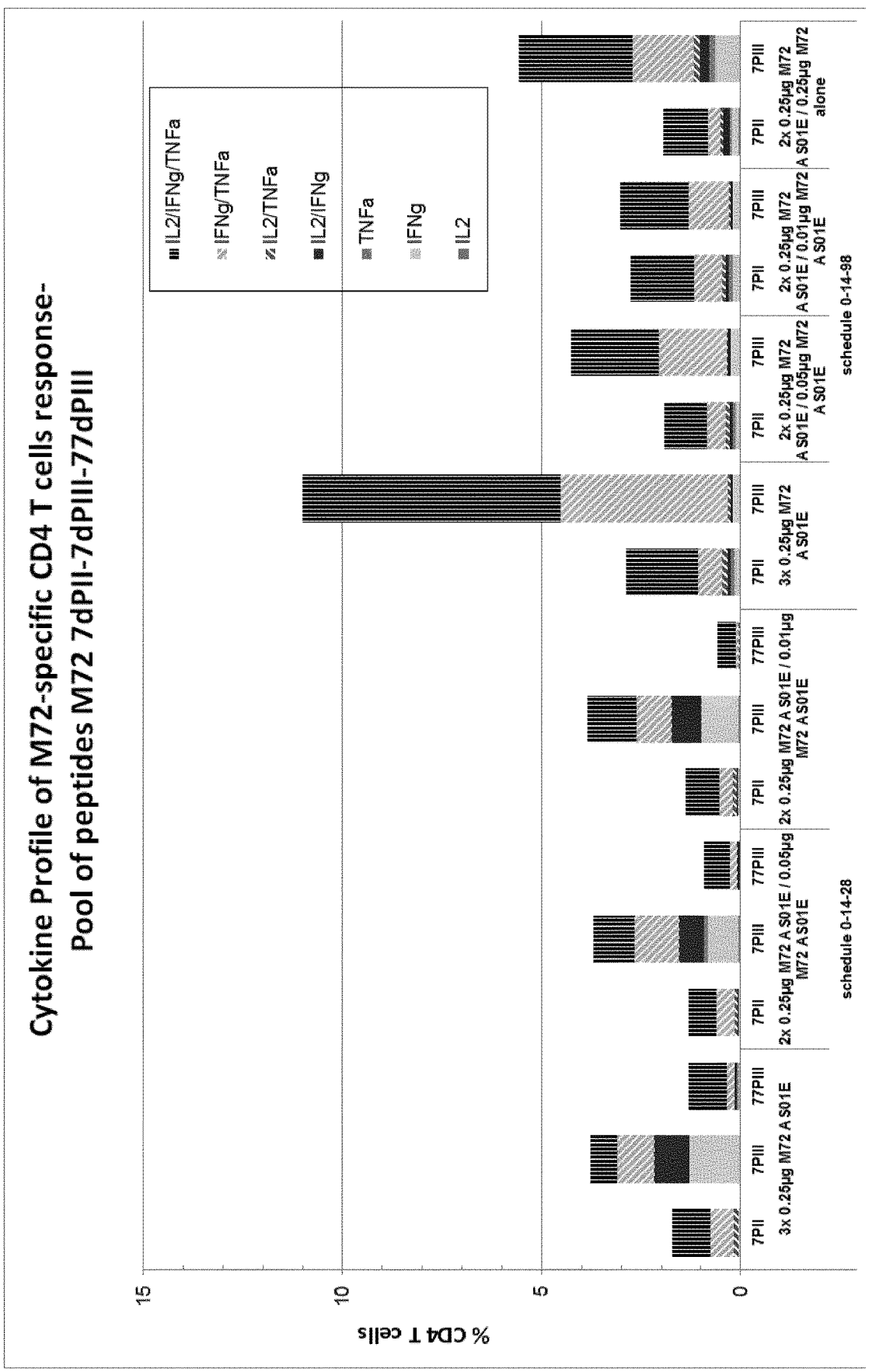
FIG. 8: CD4 T cell cytokine profile from mice administered M72 in standard and delayed regimes
Figure 9:
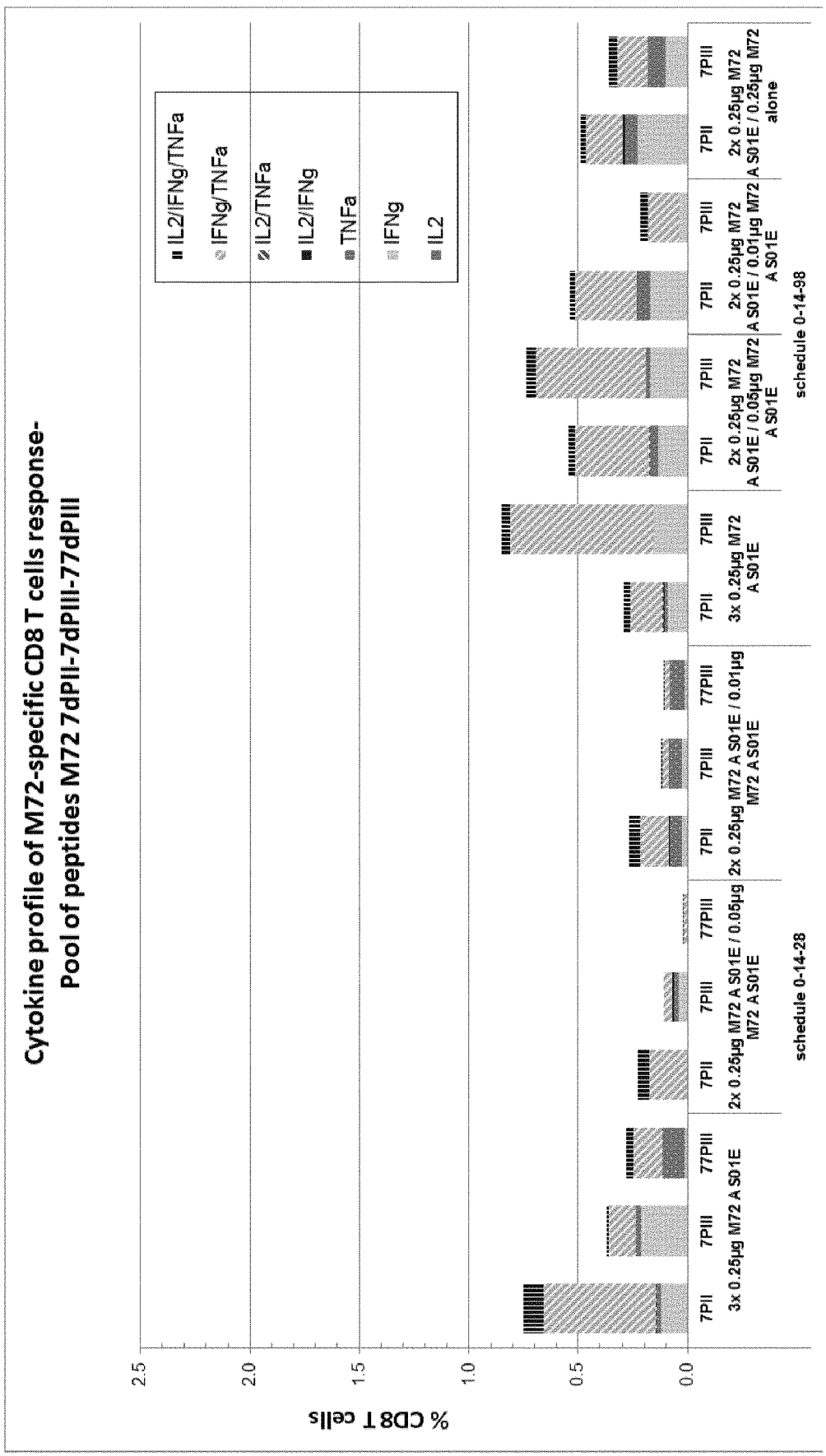
FIG. 9: CD8 T cell cytokine profile from mice administered M72 in standard and delayed regimes

Low levels of M72-specific CD8 T cells response were detected in mice that received 0.25 ug M72 dose in the standard schedule and the third immunization dose failed to boost the M72-specific CD8 T cell response (FIG. 8)

A decreased M72-specific CD8 T cell response was observed in mice that received a fractional third dose in the standard schedule. This is in line with previous data (not shown) where the CD8 T cell response was largely affected by the dose range of M72 protein used for immunizing the mice and where higher dose of M72 (1 ug or 8 ug) induced a higher level of response than 0.1 ug or 0.25 ug of M72.

In mice that received a delayed third dose of 0.25 ug of M72, a boost of the M72 specific CD8 T cell response was seen from 7PII to 7PIII in all tested pools. However, medians of the CD8 T cell response showed variability between groups at 7PII (from 0.231 to 0.817) despite the fact that all groups received 2 doses of 0.25 ug of M72/AS01E.

B. Cytokine Profile of the M72-Specific CD4 & CD8 T Cells Responses

Similar CD4 T cytokine expression profiles was observed in groups receiving a full dose, $1/5^{th}$ and $1/25^{th}$ of the dose in the standard schedule at both 7PII and 7PIII. The M72-specific CD4 T cell response included triple (IL2/IFNg/TNFa) and double (IFNg/TNFa) after 2 immunizations. The third immunization dose failed to support the progression of polyfunctional CD4 Th1 cells and instead increased the double (IL2/IFNg) and single (IFNg only) producing CD4 T cells (FIG. 7).

Figure 7:
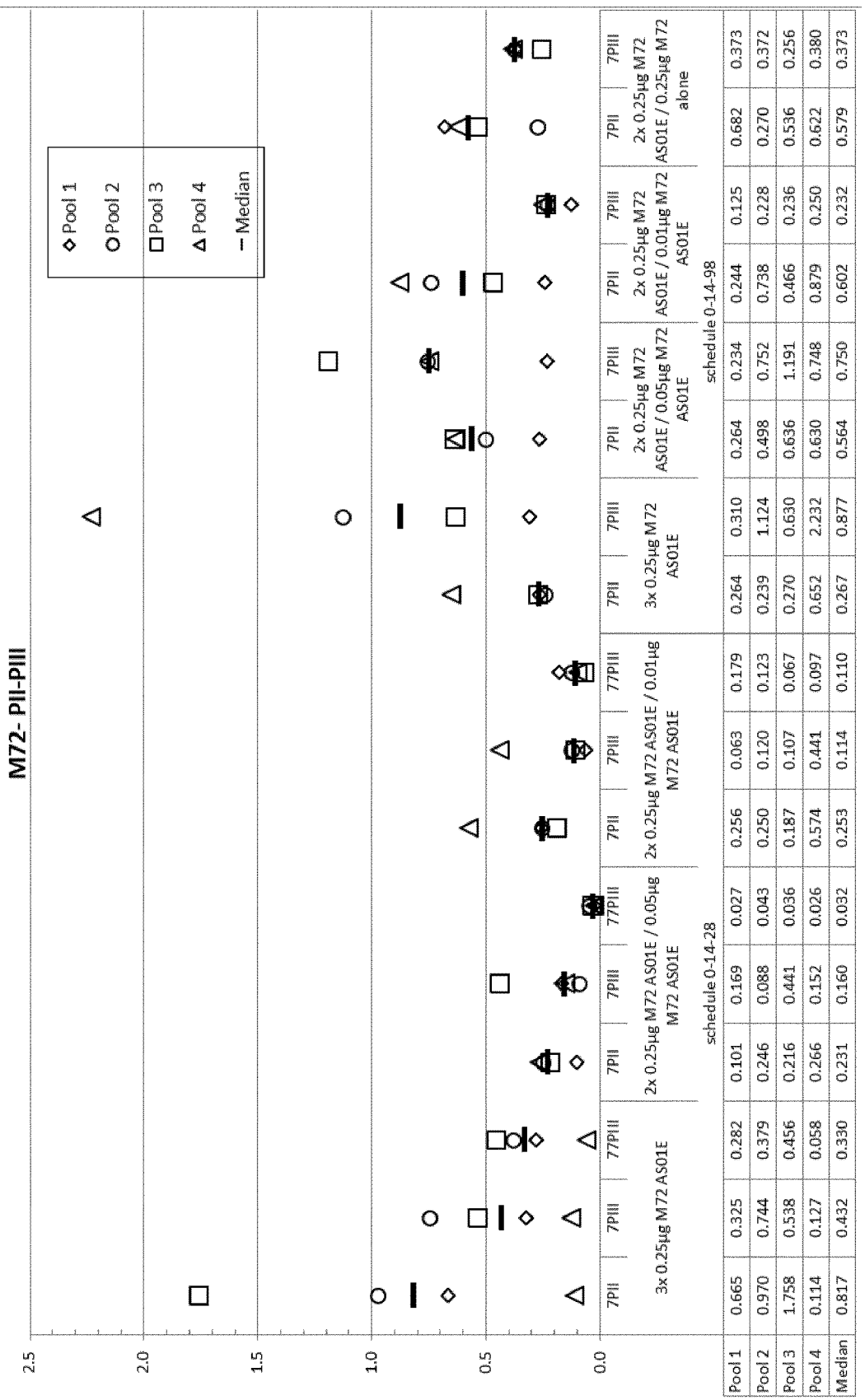
FIG. 7: CD8 T cell responses from mice administered M72 in standard and delayed regimes

Giving a delayed third dose seems to support the progression of polyfunctional CD4 Th1 cells as the M72-specific CD4 T cell response is mostly composed of IL2/IFNg/TNFa and IFNg/TNFa producing CD4 T cells (FIG. 7). AS01 further enhanced the progression of polyfunctional T cells as reduced levels of IL2/IFNg/TNFa and IFNg/TNFa and increased levels of IFNg only producing CD4 T cells were observed in mice that received a delayed and unadjuvanted third dose.

Even though the level of M72 specific CD4 T cell response in mice receiving a delayed and fractional third dose is similar to what is observed with the benchmark, the cytokine profile is slightly different and altogether these data suggests an improved progression of the polyfunctional CD4 Th1 cells in a delayed immunization schedule.

The magnitude and quality of multifunctional CD4 T cells has been shown to be a correlate of protection in mice (Derrick et al 2011 *Vaccine* 29:2902-2909).

Similar M72-specific CD8 T cell cytokine profiles were observed across all groups at both 7PII and 7PIII (FIG. 8). The M72-specific CD8 T cell responses were mostly composed of double (IFNg/TNFa) and single (IFNg only) producing CD8 T cells. Very low levels of IL2/INFg/TNFa and TNFa producing CD8 T cell were also detected.

Antibody Responses

A. Anti-M72 Ig Tot Serology

Figure 10:
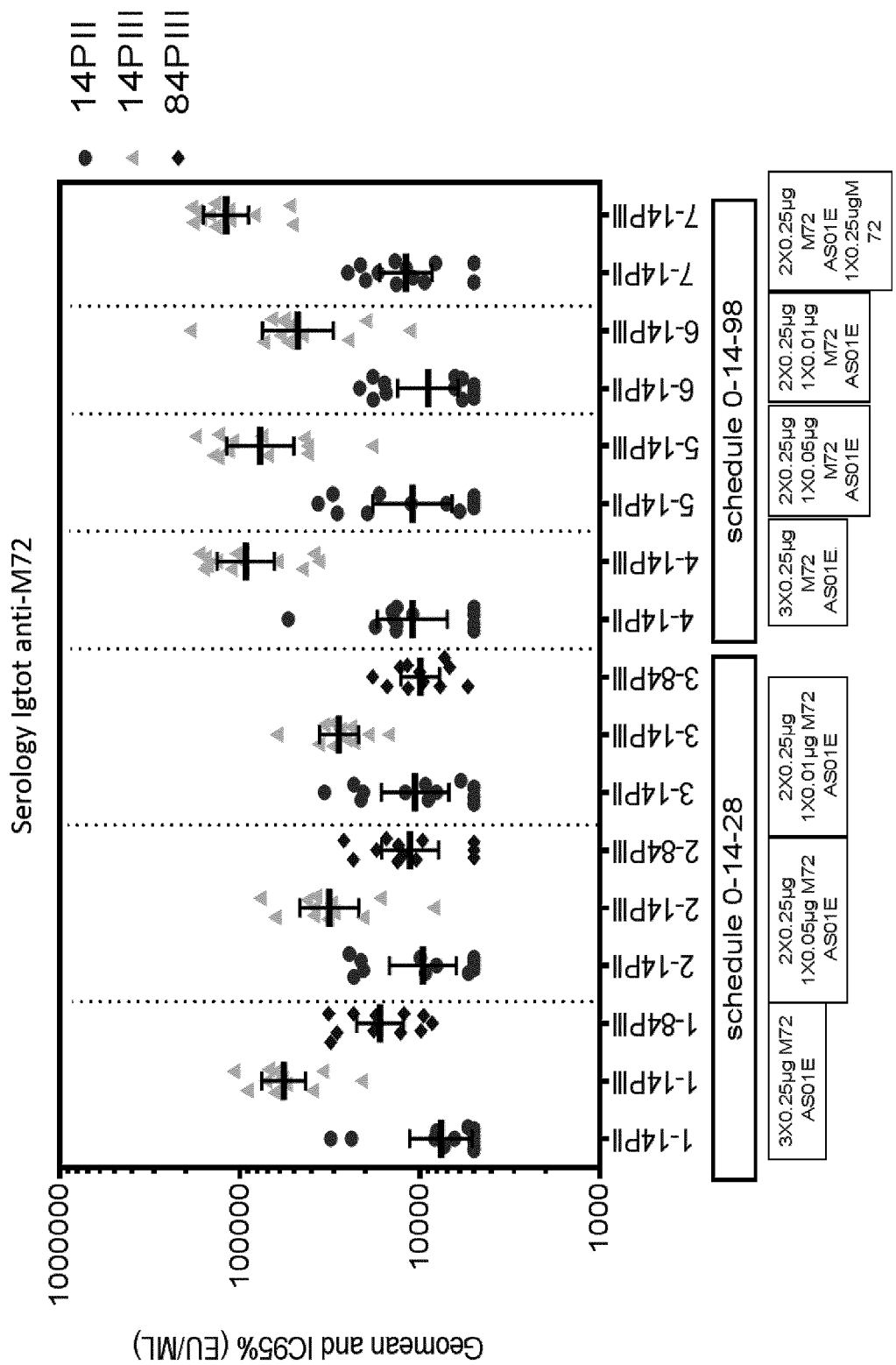
FIG. 10: Anti M72 serology from mice administered M72 in standard and delayed regimes

As shown in FIG. 10, a boost of the anti M72 serology response was observed between 14PII and 14 PIII in groups receiving a full dose, $1/5^{th}$ and $1/25^{th}$ of the dose in the standard schedule. A trend of a dose-range effect was observed with the highest dose giving the highest M72 specific serology response. The persistence of the response decreased over time as shown by the lower serology response at 84PIII.

In mice that received a delayed third immunization, a higher magnitude of the response was observed. Similar levels of M72 specific Ig were seen in the presence and absence of AS01E, suggesting that the M72 alone is sufficient to induce a high serology response after a delayed third immunization.

The invention claimed is:

1. A method for inducing an immune response against malaria in a human subject comprising administering to the subject:
   (a) a first immunogenic composition comprising RTS,S antigen and a first adjuvant, and
   (b) a second immunogenic composition comprising RTS,S antigen and a second adjuvant, wherein:
      (i) the time interval between administration of the first immunogenic composition and the second immunogenic composition is between 1 and 24 months,
      (ii) the second immunogenic composition contains between 2-50 fold lower amount of said RTS,S antigen than the first composition,
      (iii) the first and second adjuvants comprise 3D-MPL and QS21 in a liposomal formulation in the same relative proportions, and
      (iv) the second immunogenic composition contains between 2-50 fold lower amount of said liposomal adjuvant than the first immunogenic composition.

2. The method of claim 1, wherein first adjuvant and second adjuvant consist of the same components.

3. The method of claim 1, wherein the first and second adjuvants consist of the same components in the same relative proportions.

4. The method of claim 1, wherein the first and second adjuvant further comprise a sterol.

5. The method of claim 1, wherein the first adjuvant comprises between 25 and 75 micrograms of 3D-MPL and between 25 and 75 micrograms of QS21, and the second adjuvant comprises between 5 and 15 micrograms of 3D-MPL and between 5 and 15 micrograms of QS21.

6. The method of claim 1, wherein the first adjuvant comprises between 12.5 and 37.5 micrograms of 3D-MPL and between 12.5 and 37.5 micrograms of QS21, and the second adjuvant comprises between 2.5 and 7.5 micrograms of 3D-MPL and between 2.5 and 7.5 micrograms of QS21.

7. The method of claim 1, wherein the first adjuvant, the second adjuvant, or both, does not comprise aluminium.

8. The method of claim 1, wherein all antigens in the first and second immunogenic compositions are the same.

9. The method of claim 1, wherein the time interval between administration of the first immunogenic composition and administration of the second immunogenic composition is between 1 and 12 months.

10. The method of claim 1, wherein the first immunogenic composition is administered twice before administration of the second immunogenic composition.

11. The method of claim 10, wherein at a time interval of at least 1 month after administration of the second immunogenic composition, the second immunogenic composition is administered one or more further times.

12. The method of claim 1, wherein the human subject is more than 18 years of age when the first immunogenic composition is administered.

13. The method of claim 1, wherein the human subject is less than five years of age when the first immunogenic composition is administered.

14. The method of claim 1, wherein the second administration is administered intradermally.

* * * * *

SEQUENCE LISTING

```
<160> NUMBER OF SEQ ID NOS: 4

<210> SEQ ID NO 1
<211> LENGTH: 424
<212> TYPE: PRT
<213> ORGANISM: Artificial Sequence
<220> FEATURE:
<223> OTHER INFORMATION: RTS,S

<400> SEQUENCE: 1

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Lys
65                  70                  75                  80

Asn Asn Gln Gly Asn Gly Gln Gly His Asn Met Pro Asn Asp Pro Asn
                85                  90                  95

Arg Asn Val Asp Glu Asn Ala Asn Ala Asn Ser Ala Val Lys Asn Asn
                100                 105                 110
```

```
Asn Asn Glu Glu Pro Ser Asp Lys His Ile Lys Glu Tyr Leu Asn Lys
            115                 120                 125

Ile Gln Asn Ser Leu Ser Thr Glu Trp Ser Pro Cys Ser Val Thr Cys
130                 135                 140

Gly Asn Gly Ile Gln Val Arg Ile Lys Pro Gly Ser Ala Asn Lys Pro
145                 150                 155                 160

Lys Asp Glu Leu Asp Tyr Ala Asn Asp Ile Glu Lys Lys Ile Cys Lys
                165                 170                 175

Met Glu Lys Cys Ser Ser Val Phe Asn Val Val Asn Ser Ser Ile Gly
            180                 185                 190

Leu Gly Pro Val Thr Asn Met Glu Asn Ile Thr Ser Gly Phe Leu Gly
        195                 200                 205

Pro Leu Leu Val Leu Gln Ala Gly Phe Phe Leu Leu Thr Arg Ile Leu
    210                 215                 220

Thr Ile Pro Gln Ser Leu Asp Ser Trp Trp Thr Ser Leu Asn Phe Leu
225                 230                 235                 240

Gly Gly Ser Pro Val Cys Leu Gly Gln Asn Ser Gln Ser Pro Thr Ser
                245                 250                 255

Asn His Ser Pro Thr Ser Cys Pro Pro Ile Cys Pro Gly Tyr Arg Trp
            260                 265                 270

Met Cys Leu Arg Arg Phe Ile Ile Phe Leu Phe Ile Leu Leu Leu Cys
        275                 280                 285

Leu Ile Phe Leu Leu Val Leu Leu Asp Tyr Gln Gly Met Leu Pro Val
    290                 295                 300

Cys Pro Leu Ile Pro Gly Ser Thr Thr Thr Asn Thr Gly Pro Cys Lys
305                 310                 315                 320

Thr Cys Thr Thr Pro Ala Gln Gly Asn Ser Met Phe Pro Ser Cys Cys
                325                 330                 335

Cys Thr Lys Pro Thr Asp Gly Asn Cys Thr Cys Ile Pro Ile Pro Ser
            340                 345                 350

Ser Trp Ala Phe Ala Lys Tyr Leu Trp Glu Trp Ala Ser Val Arg Phe
        355                 360                 365

Ser Trp Leu Ser Leu Leu Val Pro Phe Val Gln Trp Phe Val Gly Leu
    370                 375                 380

Ser Pro Thr Val Trp Leu Ser Ala Ile Trp Met Met Trp Tyr Trp Gly
385                 390                 395                 400

Pro Ser Leu Tyr Ser Ile Val Ser Pro Phe Ile Pro Leu Leu Pro Ile
                405                 410                 415

Phe Phe Cys Leu Trp Val Tyr Ile
            420

<210> SEQ ID NO 2
<211> LENGTH: 546
<212> TYPE: PRT
<213> ORGANISM: Varicella zoster

<400> SEQUENCE: 2

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60
```

-continued

Val Asn Arg Gly Glu Ser Ser Arg Lys Ala Tyr Asp His Asn Ser Pro
 65                  70                  75                  80

Tyr Ile Trp Pro Arg Asn Asp Tyr Asp Gly Phe Leu Glu Asn Ala His
                 85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

```
Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Ile Arg Tyr Ala Ala Trp Thr Gly Gly
    530                 535                 540

Leu Ala
545
```

<210> SEQ ID NO 3
<211> LENGTH: 723
<212> TYPE: PRT
<213> ORGANISM: Artificial Sequence
<220> FEATURE:
<223> OTHER INFORMATION: M72 fusion protein

<400> SEQUENCE: 3

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285
```

```
Gly Tyr Ala Ala Ala Thr Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
            325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
    370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
            405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
            485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
            530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
            565                 570                 575

Gly Ile Val Ile Asp Pro Asn Gly Val Val Leu Thr Asn Asn His Val
        580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
            645                 650                 655

Gly Gln Gly Gly Thr Pro Arg Ala Val Pro Gly Arg Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ala
    690                 695                 700
```

-continued

Gly Gly Pro Val Val Asn Gly Leu Gly Gln Val Gly Met Asn Thr
705                 710                 715                 720

Ala Ala Ser

<210> SEQ ID NO 4
<211> LENGTH: 725
<212> TYPE: PRT
<213> ORGANISM: Artificial Sequence
<220> FEATURE:
<223> OTHER INFORMATION: M72 fusion protein (2-his)

<400> SEQUENCE: 4

Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
                20                  25                  30

Ile Arg Ser Gly Gly Ser Pro Thr Val His Ile Gly Pro Thr Ala
            35                  40                  45

Phe Leu Gly Leu Gly Val Val Asp Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
                100                 105                 110

Val Thr Trp Gln Thr Lys Ser Gly Gly Thr Arg Thr Gly Asn Val Thr
            115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
                180                 185                 190

Gly Ser Trp Ile Gly Ser Ser Ala Gly Leu Met Val Ala Ala Ala Ser
            195                 200                 205

Pro Tyr Val Ala Trp Met Ser Val Thr Ala Gly Gln Ala Glu Leu Thr
    210                 215                 220

Ala Ala Gln Val Arg Val Ala Ala Ala Tyr Glu Thr Ala Tyr Gly
225                 230                 235                 240

Leu Thr Val Pro Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
    275                 280                 285

Met Phe Gly Tyr Ala Ala Ala Thr Ala Thr Ala Thr Ala Thr Leu Leu
290                 295                 300

Pro Phe Glu Glu Ala Pro Glu Met Thr Ser Ala Gly Gly Leu Leu Glu
305                 310                 315                 320

-continued

```
Gln Ala Ala Ala Val Glu Glu Ala Ser Asp Thr Ala Ala Asn Gln
            325                 330                 335

Leu Met Asn Asn Val Pro Gln Ala Leu Gln Gln Leu Ala Gln Pro Thr
            340                 345                 350

Gln Gly Thr Thr Pro Ser Ser Lys Leu Gly Gly Leu Trp Lys Thr Val
            355                 360                 365

Ser Pro His Arg Ser Pro Ile Ser Asn Met Val Ser Met Ala Asn Asn
            370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Gln Ala Val Gln
            405                 410                 415

Thr Ala Ala Gln Asn Gly Val Arg Ala Met Ser Ser Leu Gly Ser Ser
            420                 425                 430

Leu Gly Ser Ser Gly Leu Gly Gly Val Ala Ala Asn Leu Gly Arg
            435                 440                 445

Ala Ala Ser Val Gly Ser Leu Ser Val Pro Gln Ala Trp Ala Ala Ala
            450                 455                 460

Asn Gln Ala Val Thr Pro Ala Ala Arg Ala Leu Pro Leu Thr Ser Leu
465                 470                 475                 480

Thr Ser Ala Ala Glu Arg Gly Pro Gly Gln Met Leu Gly Gly Leu Pro
            485                 490                 495

Val Gly Gln Met Gly Ala Arg Ala Gly Gly Leu Ser Gly Val Leu
            500                 505                 510

Arg Val Pro Pro Arg Pro Tyr Val Met Pro His Ser Pro Ala Ala Gly
            515                 520                 525

Asp Ile Ala Pro Pro Ala Leu Ser Gln Asp Arg Phe Ala Asp Phe Pro
530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
            565                 570                 575

Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
            595                 600                 605

Gly Gln Thr Tyr Gly Val Asp Val Val Gly Tyr Asp Arg Thr Gln Asp
            610                 615                 620

Val Ala Val Leu Gln Leu Arg Gly Ala Gly Gly Leu Pro Ser Ala Ala
625                 630                 635                 640

Ile Gly Gly Gly Val Ala Val Gly Glu Pro Val Val Ala Met Gly Asn
            645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
            675                 680                 685

Glu Thr Leu Asn Gly Leu Ile Gln Phe Asp Ala Ala Ile Gln Pro Gly
            690                 695                 700

Asp Ala Gly Gly Pro Val Val Asn Gly Leu Gly Gln Val Val Gly Met
705                 710                 715                 720

Asn Thr Ala Ala Ser
            725
```